US012788964B2

(12) United States Patent
Mitchell

(10) Patent No.: US 12,788,964 B2

(45) **Date of Patent: *Nov. 10, 2026**

(54) AXIAL COMPRESSION ASSEMBLY FOR ATTACHING TO ANATOMICAL TISSUE, SYSTEM AND METHOD

(71) Applicant: The Regents of the University of Colorado, a body, Denver, CO (US)

(72) Inventor: Max Bannister Mitchell, Castle Pines, CO (US)

(73) Assignee: Regents of the University of Colorado, a body corporate, Denver, CO (US)

(*) Notice: Subject to any disclaimer, the term of this patent is extended or adjusted under 35 U.S.C. 154(b) by 617 days.

This patent is subject to a terminal disclaimer.

(21) Appl. No.: 18/310,468

(22) Filed: May 1, 2023

(65) Prior Publication Data

US 2023/0381493 A1 Nov. 30, 2023

Related U.S. Application Data

(63) Continuation of application No. 17/466,619, filed on Sep. 3, 2021, now Pat. No. 11,684,770, and a continuation of application No. 17/173,914, filed on Feb. 11, 2021, now Pat. No. 11,123,542.

(51) Int. Cl.

*A61M 60/863* (2021.01)
*A61M 60/117* (2021.01)
*A61M 60/865* (2021.01)

(52) U.S. Cl.

CPC ........ *A61M 60/863* (2021.01); *A61M 60/117* (2021.01); *A61M 60/865* (2021.01)

(58) Field of Classification Search

CPC . A61M 60/863; A61M 60/117; A61M 60/865

See application file for complete search history.

(56) References Cited

U.S. PATENT DOCUMENTS

| | | | | |
|---|---|---|---|---|
| 3,587,115 A * | 6/1971 | Shiley | A61F 2/2427 | 623/2.38 |
| 2015/0112120 A1* | 4/2015 | Andrus | A61M 60/216 | 600/16 |
| 2016/0374674 A1* | 12/2016 | Andrus | A61B 17/064 | 606/151 |

FOREIGN PATENT DOCUMENTS

WO WO-2014145811 A1 * 9/2014 ........... A61F 2/2409

* cited by examiner

*Primary Examiner* — Ashley L Fishback

(74) *Attorney, Agent, or Firm* — Rosenbaum IP, P.C.; David G. Rosenbaum

(57) ABSTRACT

An apical cuff axial compression assembly including a ring member for coupling an apical cuff of a Ventricular Assist Device pump, to left ventricular apical tissue. Tissue anchors are employed to engage with the ring member and the apical cuff to exert direct or axial compression of the ring member to the apical cuff and to the left ventricular apical tissue. A first variant includes an axial compression ring and a plurality of openings to accommodate the tissue anchors. A second variant includes a segmented axial compression ring composed of a plurality of arcuate members, which may be contiguous or joined to each other or not. Each of the plurality of arcuate members has at least one tissue anchor opening passing there through.

19 Claims, 27 Drawing Sheets

AXIAL COMPRESSION ASSEMBLY FOR ATTACHING TO ANATOMICAL TISSUE, SYSTEM AND METHOD

CROSS-REFERENCE TO RELATED APPLICATIONS

This application is a continuation of U.S. Ser. No. 17/466,619, filed Sep. 3, 2021, which is a continuation of U.S. Ser. No. 17/173,914, filed Feb. 11, 2021, issued as U.S. Pat. No. 11,123,542, issued Sep. 21, 2021. This application is also related to U.S. Ser. No. 16,414,154, filed May 16, 2019, now U.S. Pat. No. 11,364,376, issued Jun. 21, 2022, which is a continuation of U.S. Ser. No. 16/184,452, filed Nov. 8, 2018, now U.S. Pat. No. 10,335,527, issued Jul. 7, 2019, which claims priority to U.S. Provisional Patent Application Ser. No. 62/583,030, filed on Nov. 8, 2017.

BACKGROUND

The present disclosure relates to surgical devices, systems, and methods, and more particularly to devices, systems, and methods for attaching ventricular assist devices to cardiac muscle tissue. Ventricular assist devices typically consist of a pump, a coupling that attaches the pump to cardiac muscle tissue, a conduit and a device that attaches the conduit to an arterial blood vessel, such as the aorta.

Ventricular assist devices ("VAD"), when implanted on the left side of the heart are referred to as left ventricular assist devices ("LVAD"). When a VAD is implanted on the right side of the heart it is referred to as a right ventricular assist device ("RVAD"). When a VAD is implanted on both sides of the heart it is referred to as a "Bi-VAD". For purposes of the present disclosure, unless otherwise specified, a VAD or ventricular assist device is intended to encompass LVADs, RVADs, and Bi-VADs. Use of ventricular assist devices was initially limited to heart transplant candidates as bridge devices while the patient was waiting for a donor heart. More recently, ventricular assist devices are also used as destination therapy where a patient is not a candidate for a heart transplant and requires adjunctive therapy for cardiac function insufficiency.

Most current LVAD devices are continuous flow devices, i.e., the pump operates continuously rather than in a pulsatile mode. These devices generally employ a separate cardiac muscle connector component, called an apical cuff. In the usual surgical implant, the apical cuff is first attached to the left ventricular apex, a core of cardiac muscle tissue in the center opening of the apical cuff is removed to create a blood flow conduit from the left ventricle and through the apical cuff, then the pumping device is mechanically attached to the apical cuff, and the pump outlet is connected to the aorta, typically by a tubular graft. Rarely, the apical cuff and VAD pump is attached to the right atrium or right ventricle in circumstances where right ventricular or single ventricular VAD support is desired. Most conventional apical cuffs consist of a rigid metal fitting and a fabric sewing skirt coupled to the rigid metal fitting. The sewing skirt is sutured to the cardiac muscle tissue about a circumference of the fabric sewing skirt, and the pump is connected by mechanically mating it to the rigid metal fitting. The circumferential sutures provide radial compression between the cardiac muscle tissue and the fabric sewing skirt.

Conventional installation methods for apical cuffs generally involve attaching the apical cuff to the left ventricular apex with surgically placed sutures that are brought through the sewing skirt on the apical cuff. For example, a practitioner may utilize a plurality of horizontal mattress double-armed pledgeted sutures placed from the epicardial surface of the left ventricular myocardium toward the sewing skirt on the apical cuff. Each needle is passed through the heart and then up through the sewing skirt. After all sutures are placed, the sutures are successively tied resulting in knots on the sewing skirt. After the apical cuff is attached to the heart, a core of left ventricular muscle is removed through the center of the apical cuff, and the pump is mechanically fastened to the apical cuff. This conventional method/practice of placing pledgeted sutures is time consuming, and imperfections may result in significant bleeding complications.

The prior co-pending and commonly assigned patent and patent application referenced above sought to address deficiencies in conventional apical cuff attachment and methods by providing an implantable assembly having a connection interface that engages the apical cuff, a plurality of outer plates, and a plurality of connectors that extend between and interconnect the connection interface with the plurality of outer plates. When implanted, the connection interface engages the apical cuff of the VAD, the plurality of outer plates are engaged to the cardiac tissue in a position radially spaced from the connection interface, and the plurality of connectors extend radially from the connection interface and connect to the plurality of outer plates. Once the connection interface is secured to the apical cuff and the cardiac tissue and the plurality of outer plates are secured to the cardiac tissue, the plurality of outer plates are displaced radially inward on the plurality of connectors and toward the connection interface until hemostasis is achieved.

This prior device and method requires axial securing of the interface connector to the apical cuff and cardiac tissue, axial securing of the plurality of outer plates to the cardiac tissue, and radial securing of the outer plates to the interface connector.

The need exists, therefore, for a simpler apical cuff anastomotic assembly that employs axial compression to both secure the apical cuff to the cardiac tissue and achieve hemostasis at the implant site enabling the surgeon to implant the apical cuff anastomotic assembly with fewer steps, more efficiently, and with less trauma to the patient and to the heart.

SUMMARY

In variants of the present disclosure, there is provided one or more surgical devices, systems, and methods that address one or more of the shortcomings of the conventional apical cuff devices that are affixed to the heart muscle by suturing. In its variants, the present disclosure provides an implantable anastomotic assembly that is configured to be attached to cardiovascular tissue, particularly, the left ventricular apex. The implantable anastomotic assembly of the present disclosure employs a ring member that couples to the VAD apical cuff and engages the sewing skirt to affix the apical cuff to the left ventricular tissue. Tissue anchors, synonymously termed herein as affixation members, engage with the ring member and the sewing skirt to exert direct or axial compression of the ring member through the sewing skirt of the apical cuff and to the left ventricular apical tissue.

In a first variant of the present disclosure, there is provided a ring member, synonymously termed herein an axial compression ring, having a plurality of openings passing axially through the ring member. At least some of the plurality of openings are configured to receive an affixation member there through. Optionally, at least some of the plurality of openings may be provided to reduce the mass of the ring member and/or as suture openings to allow supplemental suturing of the ring member through the sewing skirt and into the apical myocardium.

In a second variant of the present disclosure, the ring member is comprised of a plurality of arcuate members, synonymously termed herein as axial compression plates, each arcuate member subtends a fractional part of the circumference of the ring member. Each of the plurality of arcuate members has at least one opening passing axially there through and is configured to receive an affixation member through the at least one opening. Like with the first variant, each of the plurality of arcuate members may have additional openings passing axially through the arcuate member that reduce the mass of the arcuate member and/or which are configured to accept sutures or other affixation members to secure the arcuate member through the sewing skirt and to the myocardial tissue.

In a third variant of the present disclosure, there is provided an affixation member or tissue anchor configured as a helical screw configured to engage with the affixation member openings of either the axial compression ring or the axial compression plates. The helical screw is a pig-tail type screw having a helical coil projecting from a screw cap, with a distal end of the helical coil, i.e., the end opposite the screw head, terminating in a tapered point configured to penetrate myocardial tissue. The screw cap may have a tapered sidewall, an upper surface having either an internal driver engagement, such as a driver recess, or an external driver engagement about the periphery of the screw cap. In either the internal or external driver engagement configurations, the screw cap is configured to engage with a driver to apply a torsional force to the helical screw. Where the internal driver engagement, e.g., a driver recess, is employed, it may have any of a large number of known configurations, including, without limitation, slotted, cruciform, internal polygonal, hexalobular, three-pointed, or tamper resistant, such as, for example, pentalobe. Similarly, where an external driver engagement is provided, the driver cap, itself, may have any of a large number of known configurations, such as regular or irregular polygonal shapes, e.g., triangular, quadrilateral, pentagonal, hexagonal, etc. Combinations of both internal and external driver engagements are also contemplated and intended by the present disclosure.

The screw cap may have a recess in its lower surface to receive an upper end of the helical coil or the lower surface may be substantially planar. In either case, the upper end of the helical coil may be planarized and joined with the lower surface, by a wide variety of known methods.

The affixation member may also be configured as other types of connectors other than a helical screw configuration. For example, the affixation member may be a surgical staple, an expandable pin, a shape memory staple, shape memory pins, or other types of affixation members configured to exert an axially compressive force to the ring member.

In a fourth variant of the present disclosure, there is provided a delivery tool and loading tray for the first variant of the present disclosure. The loading tray of the fourth variant has a base bounded by a plurality of arcuate projections that extend from an upper surface of the base and circumferentially bound the base defining a recess bounded by the upper surface of the base and the plurality of arcuate projections. A bore passes centrally through the base and terminates in a tubular projection extending from a lower surface of the base. The plurality of arcuate projections are in spaced apart relationship about the circumference of the loading tray. A plurality of openings pass axially through the base and are circumferentially spaced about the bore. The plurality of openings are spaced to match the spacing of the affixation member openings of the ring member. The delivery tool has a generally cylindrical shape having a plurality of lobular projections extending radially outward from an upper lateral surface of the delivery tool and a plurality of semi-circular recesses in a lower lateral surface of the delivery tool. Each of the plurality of lobular projections is in axial alignment with a corresponding semi-circular recess and has a driver opening passing axially there through that communicates with the semi-circular recess immediately adjacent the lobular projection. Again, each of the driver openings and each of the semicircular recesses are in spaced apart relationship about a circumference of the delivery tool, with the spacing corresponding to match the spacing of the affixation member openings of the ring member. Alignment projections may optionally be provided on the delivery tool that engage with recesses in the loading tray to ensure axial alignment of the plurality of driver openings, plurality of semicircular recesses, plurality of affixation member openings, and plurality of openings in the base of the loading tray.

In operation, the apical cuff, having the sewing skirt joined thereto, and the axial compression ring member of the present invention are joined together and placed into the loading tray. The affixation member openings are aligned with the each of the plurality of openings in the base of the loading tray. A plurality of helical screws are loaded into the semi-circular recesses of the delivery tool, and the delivery tool is engaged with the loading tray such that the semi-circular recesses and helical screws are in axial alignment with the affixation openings of the ring member and the openings in the base of the loading tray. Once brought into engagement with the loading tray, a driver, such as a screwdriver, is inserted into each of the driver openings in the delivery tool and actuated to drive each of the helical screws into and through a corresponding affixation member opening, and into the sewing skirt on the apical cuff. It is preferable, though optional, to drive the helical screws through the sewing skirt such that it protrudes from an opposing surface of the sewing skirt and the tip of the affixation member is visible when viewed through the corresponding and axially aligned opening in the base of the loading tray. Each of the tissue anchors may be driven individually in sequence or more than one or all of them may be driven simultaneously. In this manner, the apical cuff, sewing skirt, ring member and tissue anchors are all preloaded in the delivery tool for implantation to the myocardial tissue.

In a fifth variant of the present disclosure, there is provided a delivery tool and loading tray for the second variant of the present disclosure. Like the delivery tool and loading tray for the first variant, the delivery tool of the second variant has a generally cylindrical shape and has a plurality of lobular projections extending radially outward from an upper lateral surface of the delivery tool and a plurality of semi-circular recesses in a lower lateral surface of the delivery tool. Each of the plurality of lobular projections is in axial alignment with a corresponding semicircular recess and has a driver opening passing axially there through that communicates with the semi-circular recess immediately adjacent the lobular projection. Each of the plurality of driver openings and each of the plurality of semicircular recesses are in spaced apart relationship about a circumference of the delivery tool, with the spacing corresponding to match the spacing of the affixation member openings of the each of the plurality of arcuate members comprising the ring member. The loading tray of the fifth variant has a base with a central opening passing axially through the base, and a recess in the loading tray. A plurality of openings pass through the base and are circumferentially positioned about the central opening passing axially through the base. The plurality of openings are spaced to match the spacing of the affixation member openings in each of the plurality of arcuate members of the ring member. At least one circumferential wall projection extends upwardly from the base and bounds the recess in the loading tray. Optionally, alignment projections may be provided on the delivery tool that engage with recesses in the circumferential wall projection to ensure axial alignment of the plurality of driver openings, plurality of semicircular recesses, plurality of affixation member openings, and plurality of openings in the base of the loading tray.

In operation, like with the fourth variant of the disclosure, in the fifth variant of the disclosure, the apical cuff, which includes the sewing skirt, and the arcuate members of the present invention are joined together and placed into the loading tray. The plurality of arcuate members are positioned on the apical cuff in a spaced apart circumferential fashion. The affixation member openings in each of the plurality of arcuate members are aligned with the each of the plurality of openings in the base of the loading tray. A plurality of tissue anchors are loaded into the semi-circular recesses of the delivery tool, and the delivery tool is engaged with the loading tray such that the semi-circular recesses and affixation members are in axial alignment with the affixation openings in the arcuate members and the openings in the base of the loading tray. Once brought into engagement with the loading tray, a driver, such as a screwdriver, is inserted into each of the driver openings in the delivery tool and actuated to drive the actuation members into and through a corresponding affixation member opening, through the sewing skirt on the apical cuff and into each of the corresponding openings in the base of the loading tray. In this manner, the apical cuff, sewing skirt, axial compression plates and tissue anchors are all pre-loaded in the delivery tool for implantation to the myocardial tissue.

The forgoing features and elements may be combined in various combinations without exclusivity, unless otherwise expressly indicated herein. These features and elements, as well as the operation of the disclosed embodiments, will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

DETAILED DESCRIPTION

Figure 1:
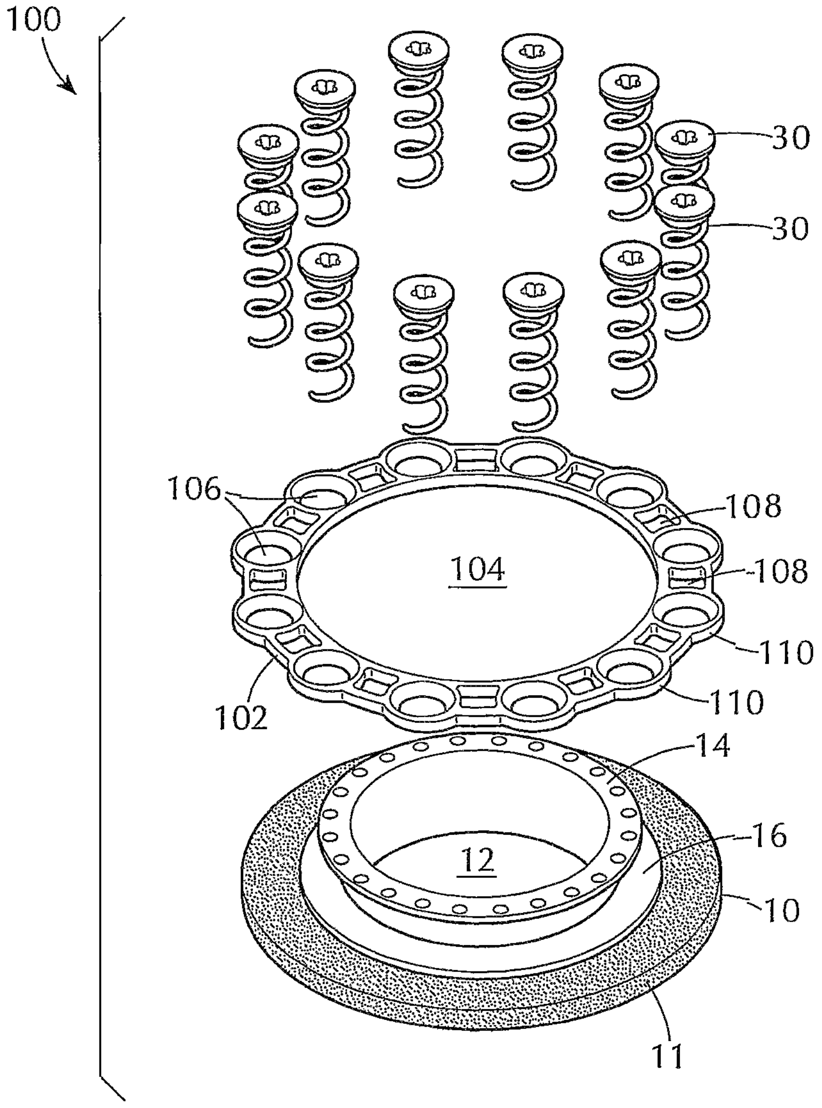
FIG. 1 is an exploded perspective view of the apical cuff axial compression attachment assembly in accordance with a first embodiment of the present disclosure.

The device, system and methods of the present invention will be described with reference to certain exemplary embodiments thereof. These exemplary embodiments are intended to be illustrative and non-limiting examples of the present invention. The example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. Those of ordinary skill in the art will understand and appreciate that variations in materials, structure, material properties, and tolerances may be made without departing from the scope of the invention, which is defined only by the claims appended hereto and their range of equivalents. In some example embodiments, well-known processes, well-known device structures, and well-known technologies are not described in detail.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching when used throughout the figures to denote different parts but not necessarily to denote the same or different materials.

For ease of understanding, the present invention is described with reference to the accompanying Figures. In the accompanying Figures like elements are identified by like reference numerals.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including" and "having," are inclusive and therefore specify the presence of stated features, integers, steps, operations, elements and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms such as "inner," "outer." "beneath," "below," "lower," "above," "upper," and the like, may be used herein for ease of description to describe one element or feature's relationship to another element(s) or features) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than and including totally.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods, and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Turning now to the accompanying Figures, there are shown alternative embodiments of the apical cuff axial compression attachment assembly, tissue fixation devices for the same, and systems and apparatus for loading and delivering the apical cuff axial compression attachment assemblies and methods thereof. While the present disclosure references alternative embodiments of the apical cuff axial compression attachment assembly with reference to two variants of the HEARTMATE 3 (Abbott, Abbott Park, Illinois, USA) LVAD apical cuff, it will be understood that the illustrated and exemplary embodiments of the apical cuff axial cuff attachment assemblies, tissue fixation devices, systems and apparatus and methods thereof described herein are intended to apply to any other VAD device and apical cuff. The HEARTMATE 3 has two commercially available apical cuffs, one which is referred herein to as a "standard cuff" and one which is referred to herein as a "mini cuff." It will be understood by those skilled in the art that while the mini-cuff and standard cuff HEARTMATE 3 apical cuffs are used as examples of the present invention, other apical cuffs, such as, for example and without limitation, the HEARTWARE HVAD (Medtronic, Minneapolis, Minnesota, USA), or others may be used with the present invention.

Apical cuffs are employed to act as a connecting device to which the VAD pump is mechanically fastened. Apical cuffs are first implanted by means of surgically placed sutures in the heart wall, and fluid flow communication is established through an inflow cannula in the apical cuff and between the heart chamber and the VAD pump. The present invention has two variants of apical cuff axial compression attachment assemblies. A first one is an assembly for the HEARTMATE 3 mini-cuff, while a second one is an assembly for the HEARTMATE 3 standard cuff. Both the mini-cuff and the standard cuff variants of the HEARTMATE 3 LVAD apical cuffs have the same VAD pump attachment mechanism and cannula diameter but differ in the configuration of a lower flange that abuts a sewing skirt. The mini-cuff connector is closely related to an apical cuff shown in FIG. 33 U.S. Pat. No. 9,981,076 (the "'076 Patent") while the standard cuff connector is closely related to the apical cuff shown in FIG. 63A of the same '076 patent. The '076 patent is hereby incorporated by reference in its entirety as teaching an exemplary apical cuff which may be employed with the present disclosure.

As illustrated in FIG. 1, a mini-cuff apical cuff 10 includes a ring having an upper flange 14 that engages and couples with the VAD pump (not shown), a lower flange 16 that carries a sewing skirt 11, and a central opening 12 that allows fluid flow through the mini-cuff apical cuff 10. The sewing skirt 11, which may consist of one or more layers of a felt, mesh, woven, non-woven or other material or fabric, including, without limitation, polytetrafluoroethylene (PTFE), polyethylene terephthalate (PET) (e.g., Dacron), polyester or other similar biocompatible material suitable for both suture retention, blood absorption and hemostatic properties, is joined to the lower flange 16 such as by a silicone or other biocompatible adhesive. Conventional apical cuffs, such as mini-cuff 10 or standard cuff 20, typically have a sewing skirt 11, 21, respectively.

Conventionally, after the patient is placed on cardiopulmonary bypass, the apical cuff is placed using sutures placed through the heart muscle and into the sewing skirt 11. Then the heart muscle is cored, and the VAD pump mechanically attached to the apical cuff.

Consistent with an embodiment of the present disclosure, there is provided an apical cuff axial compression attachment assembly 100 that consists of an axial compression ring 102 having a central annular opening 104 configured to concentrically engage over the ring of the mini-cuff 10 and seat against the sewing skirt 11 and adjacent the lower flange 16 of the mini-cuff 10. The axial compression ring 102 has a plurality of primary openings 106 and, optionally, may have a plurality of secondary openings 108. The plurality of primary openings 106 may have a generally circular transverse cross-sectional shape and, optionally, may each have a radially inward taper to the walls of the primary openings 106. The secondary openings 108, where provided, are positioned between adjacent pairs of primary openings 106 and may serve to reduce the mass of the axial compression ring 102 and/or as supplemental suture openings. The central opening 104 preferably has a regular circular opening profile with the inner diameter dimensioned to concentrically abut the outer diameter of the lower flange 16 of the apical cuff 10. An outer peripheral surface of the axial compression ring 102 may have a regular, such as a circular profile, or an irregular profile, such as scalloped or rounded surfaces defining a portion of the outer perimeters of each of the primary openings 106 and secondary openings 108.

Optionally a concentric ring consisting of one or more layers of a felt, mesh, woven, non-woven or other material or fabric, including, without limitation, polytetrafluoroethylene (PTFE), polyethylene terephthalate (PET)(e.g., Dacron), polyester or other similar biocompatible material suitable for both suture retention, blood absorption and hemostatic properties having a thickness equal to the thickness of the apical cuff sewing skirt 11 and may be bonded to the lower surface of the apical compression ring using one or more methods of fixation such as sutures, silicone or other biocompatible adhesive such that in the installed state the inner radius of the ring abuts the perimeter of the sewing skirt 11 of the apical cuff 10 and the outer perimeter of the ring extends outside the primary openings 106 of the compression ring 102. This optional feature provides additional material for tissue anchor 30 engagement to enhance hemostasis and prevent abrasion of the outer perimeter of the axial compression ring against the myocardial surface.

A plurality of tissue anchors 30 are also provided with the apical cuff axial compression attachment assembly 100. Each of the plurality of tissue anchors 30 is configured to seat against the axial compression ring 102 and pass through the plurality of primary openings 106 and the sewing skirt 11 of the apical cuff 10. When fully seated against the heart muscle, the plurality of tissue anchors 30 embed into the myocardium of the heart muscle and axially compress the axial compression ring 102 and the sewing skirt 11 against the heart muscle. In this manner, the apical cuff 10 is secured in a hemostatic manner against the heart muscle and prevented from torsional rotation by the tissue anchors 30.

Figure 2:
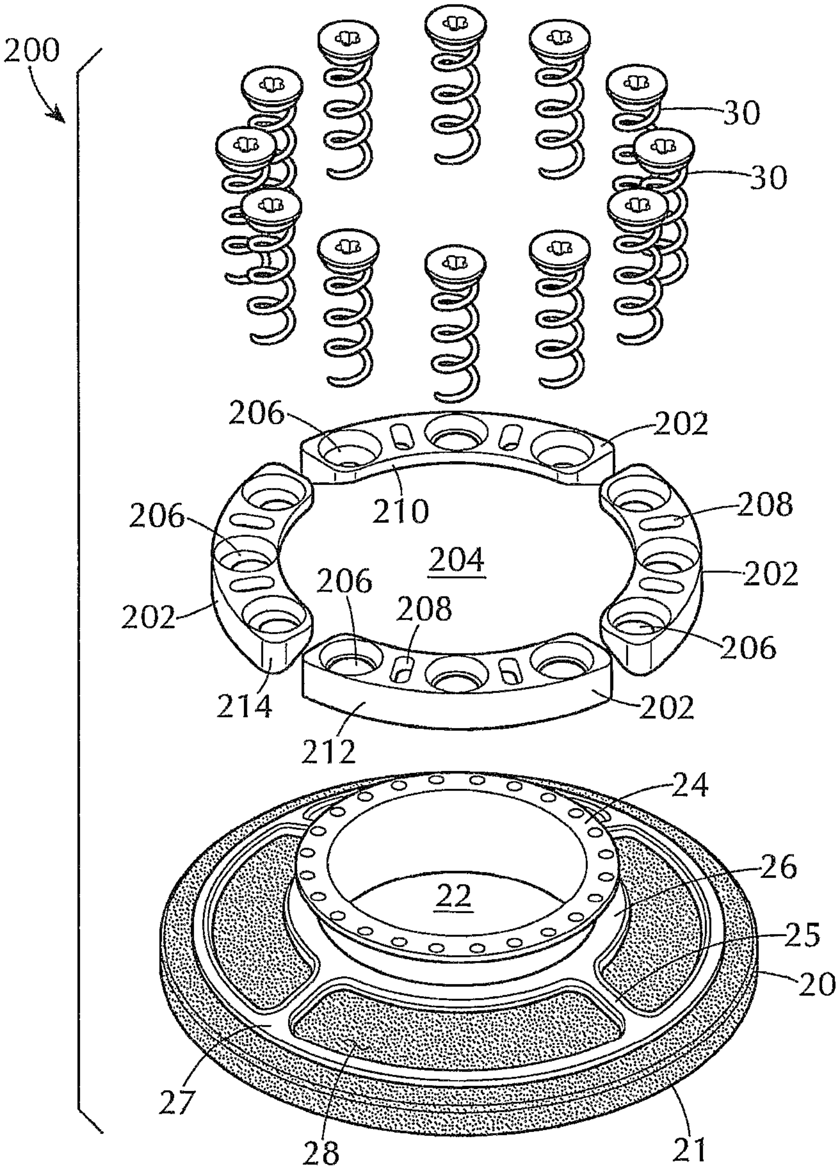
FIG. 2 is an exploded perspective view of the apical cuff axial compression attachment assembly in accordance with a second embodiment of the present disclosure.

In accordance with a second embodiment of the present disclosure, there is provided an apical cuff axial compression attachment assembly 200 which is configured to affix a standard cuff 20, such as that provided with the HEARTMATE 3, as illustrated in FIG. 2. The standard cuff 20 is similar to the mini-cuff 10 in that it consists of an upper flange 24 that engages and couples with the VAD pump (not shown), a lower flange 26 that carries a sewing skirt 21, and a central opening 22 that allows fluid flow through the standard cuff 20. The sewing skirt 21, which also may consist of one or more layers of a felt, mesh, woven, non-woven or other material or fabric, including, without limitation, polytetrafluoroethylene (PTFE), polyethylene terephthalate (PET) (e.g., Dacron), polyester or other similar biocompatible material suitable for both suture retention, blood absorption and hemostatic properties, is joined to the lower flange 26 mechanically or by adhesive, such as silicone or other biocompatible adhesive. Unlike the mini-cuff 10, the standard cuff 20, includes an outer ring 27 that is joined to the lower flange 26 by a plurality of radial arms 25 that retain the outer ring 27 in a spaced apart relationship relative to the lower flange 26. The plurality of radial arms 25 extend radially outward from the lower flange 26 and project in a generally downward direction away from the upper flange 24 and the lower flange 26, and bear against the sewing skirt 21, causing the sewing skirt 21 to assume a generally downward bias away from the lower flange 26 and toward the heart muscle. The plurality of radial arms 25 are radially spaced about the circumference of the lower flange 26 forming arcuate openings 28 that extend circumferentially between adjacent pairs of the plurality of radial arms 25 and pass through the space between the lower flange 26 and the outer ring 27.

A plurality of axial compression plates 202, also referred to synonymously herein as arcuate members 202, are provided and each subtends an arcuate section of a 360-degree ring structure to form a central annular opening 204 configured to concentrically engage around the ring of the standard cuff 20, seat within the arcuate openings 28, and seat against the sewing skirt 21. Each of the plurality of axial compression plates 202 has an inner plate wall 210 on the inner radius of the axial compression plate 202, an outer plate wall 212 on the outer radius of the axial compression plate 202, and plate end walls 214 at opposing ends of each axial compression plate 202. Optionally, each of the plurality of axial compression plates 202 may have a depth that is radially tapered such that the depth at the outer plate wall 212 is greater than the depth of at the inner plate wall 210. The taper of the depth of the axial compression plates 202 may have a slope on its lower surface, i.e., that facing the sewing skirt 21, that is optionally configured to correspond to the slope of the plurality of arms 25 extending from the lower flange 26 to the outer ring 27 of the apical cuff 20. Where the axial compression plates 202 have a slope on their lower surfaces, an upper surface of each axial compression plate 202 is preferably non-sloped to ensure seating and apposition between the tissue anchors 30 and the primary openings 206 and axial compression of the axial compression plates 202 with the sewing skirt 21 and the heart muscle (not shown).

Each of the plurality of axial compression plates 202 has at least one of a plurality of primary openings 206 and, optionally, may have a plurality of secondary openings 208. Like with the axial compression ring 102, the plurality of primary openings 206 may have a generally circular transverse cross-sectional shape and, optionally, may each have a radially inward taper to the walls of the primary openings 206. The secondary openings 208, where provided, are positioned between adjacent pairs of primary openings 206 and may serve to reduce the mass of each axial compression plate 202 and/or as supplemental suture openings.

While the present disclosure includes compression ring 102 or compression plates 202 as discrete elements separate from the apical cuff 10, 20, it will be understood and appreciated by those skilled in the art that the apical cuff 10, 20 itself may be modified to include equivalents of compression ring 102 or compression plates 202 which are integral with and part of the apical cuff 10, 20, respectively. For example, the lower flange 16 of apical cuff 10 may be radially extended to project circumferentially further over the sewing skirt 11 and have a plurality of primary openings 106 arrayed about the radially extended portion of the lower flange 16 to accommodate tissue anchors 30 to pass through each of the primary openings 106 and engage with and pass through the sewing skirt 11. Alternatively, the compression ring 102 may simply be affixed to or joined with the lower flange 16 of apical cuff 10 to effectively diametrically enlarge the lower flange 16 of the apical cuff 10. Similarly, the lower flange 26, arcuate openings 28, and outer ring 27 of apical cuff 20 may be modified by eliminating the arcuate openings 28 and reconfiguring them as primary openings 206 that are configured to accommodate tissue anchors 30 to pass through each of the primary openings 206 and engage with and pass through the sewing skirt 21, thereby axially compressing the apical cuff 20 and the sewing skirt 21 to the target tissue. Alternatively, the plurality of compression plates 202 may be fixedly or removably joined or coupled to the lower flange 26, the outer ring 27, and the radial arms 25 such that axial compression of the plurality of compression plates 202 transmits an axially compressive force to the apical cuff 20 itself and distributes the compressive force about a substantially circumferential extent of the lower flange 26, outer ring 27 and radial arms 25 against the sewing skirt 21 and the target tissue. Alternatively, a plurality of arcuate members 202 may be bonded or otherwise joined directly to or within the sewing skirt 21.

Like with apical cuff axial compression attachment assembly 100, a plurality of tissue anchors 30 are also provided with the apical cuff axial compression attachment assembly 200. Each of the plurality of tissue anchors 30 is configured to seat against the plurality of axial compression plates 202 and pass through the plurality of primary openings 206 and the sewing skirt 21 of the apical cuff 20. When fully seated against the heart muscle, the plurality of tissue anchors 30 pass through the sewing skirt 21 and embed into the myocardium of the heart muscle and axially compress the axial compression plate 202 and the sewing skirt 21 against the heart muscle. In this manner, the apical cuff 20 is secured in a hemostatic manner against the heart muscle and prevented from torsional rotation by the tissue anchors 30.

Figure 3:
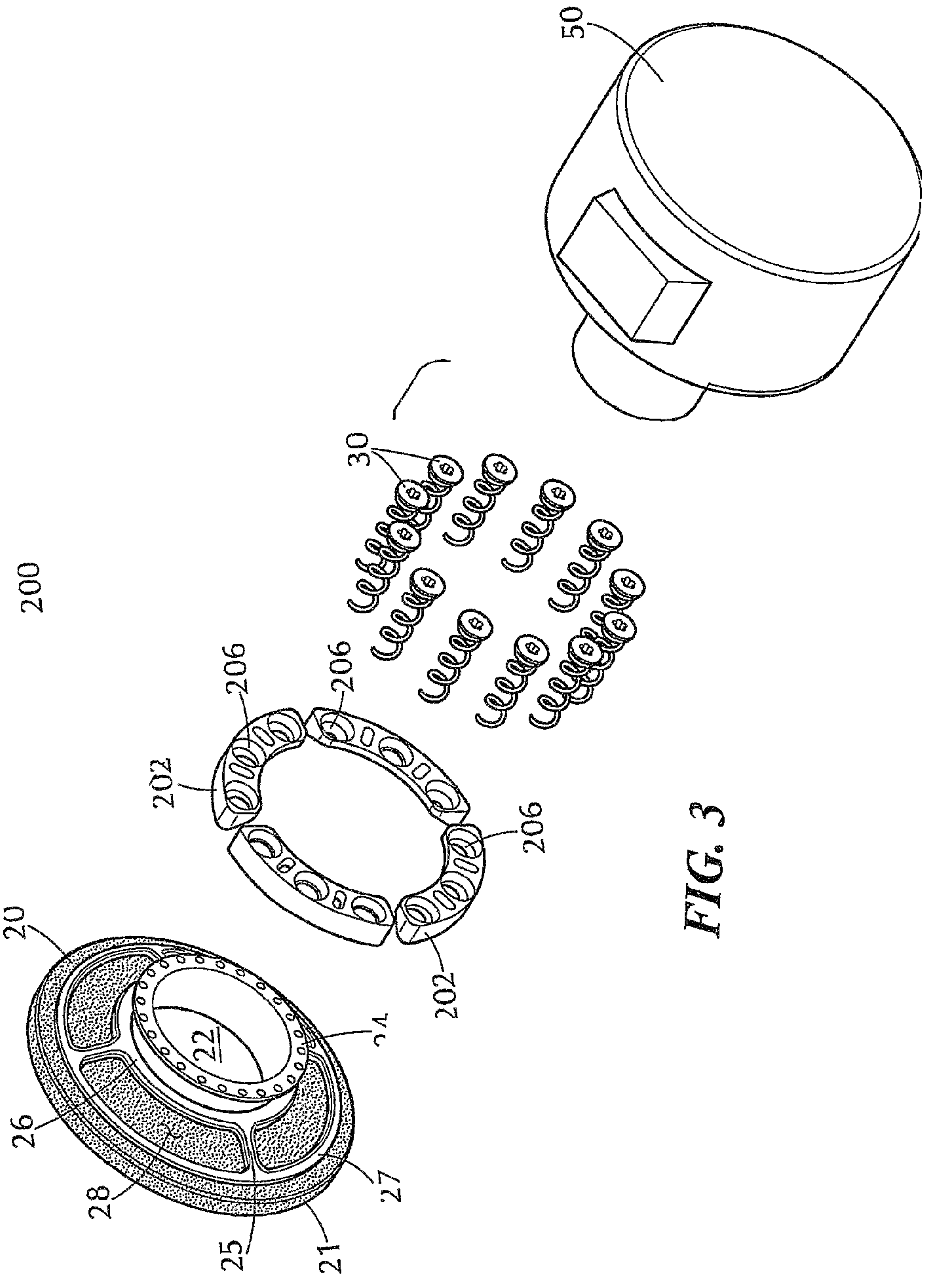
FIG. 3 is an exploded perspective view of the second embodiment of the apical cuff axial compression attachment assembly showing a VAD pump.

FIG. 3 illustrates a VAD pump 50 in exploded alignment with the apical cuff axial compression attachment assembly 200. Those skilled in the art will appreciate that VAD pump has a conduit projection that fluidly couples with the central opening 22 of the apical cuff 20, and then engages the upper flange 24 of the apical cuff 20 to lock the VAD pump 50 to the apical cuff. This attachment mechanism is illustrated in the '076 patent incorporated by reference.

Figure 4A:
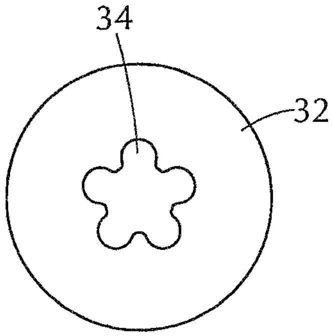
FIG. 4A is a top elevational view of a helical screw in accordance with the present disclosure.
Figure 4B:
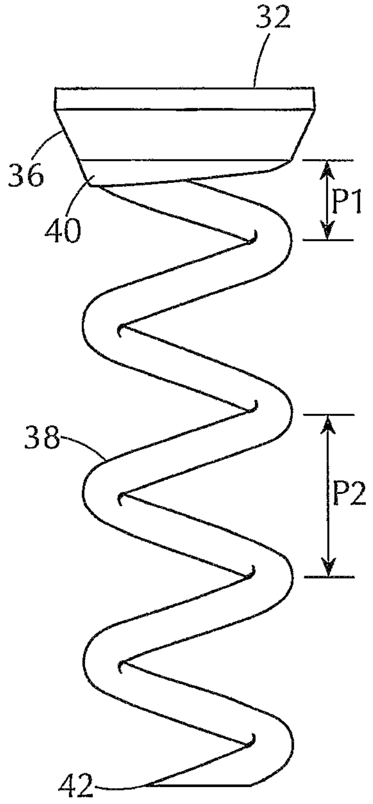
FIG. 4B is a side elevational view of the helical screw in accordance with the present disclosure.
Figure 5:
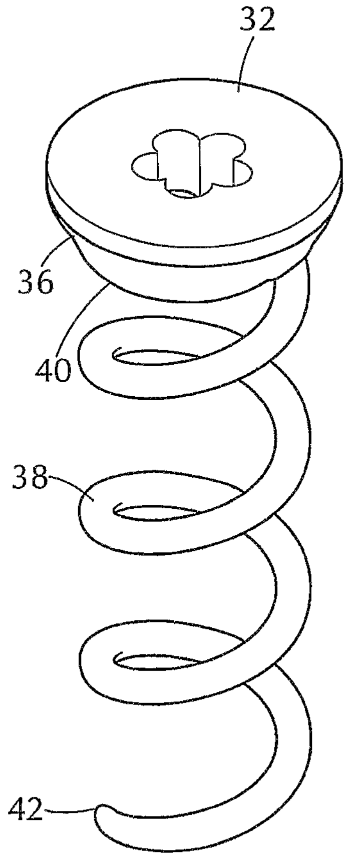
FIG. 5 is a perspective view of the helical screw in accordance with the present disclosure.

FIGS. 4A-5 illustrate a tissue anchor 30 in accordance with the present disclosure. In accordance with an embodiment of the present disclosure, tissue anchor 30 includes a tissue anchor head 32, a tissue anchor head body 36, a driver engagement 34, and a helical coil 38 that terminates in a tapered distal end 42. The helical coil 38 also has a proximal end 40 that is joined to or coupled with the tissue anchor head 32. The junction or coupling between the tissue anchor head 32 and the proximal end 40 of the helical coil 38 may be made by welding, adhesive, embedding, interference fit, or other methods of joining similar or dissimilar material as are known in the art. The anchor head body 36 consists of a tapered or non-tapered portion that projects distally from the anchor head 32. The anchor head body 36 may be solid such that its distal surface, i.e., the surface to which the proximal end 40 of helical coil 38 joins or couples, is substantially planar, or anchor head body 36 may have a distal recess bounded by tapered or non-tapered wall surfaces. The helical coil 38 is preferably formed of a helical winding of a cylindrical wire member and has a first winding pitch P1 at the proximal end of the helical coil 38 and a second winding pitch P2 along the remainder of the length of the helical coil 38 to the tapered distal end 42. First winding pitch P1 is configured to allow for stiffness at the proximal end of helical coil 38, while second winding pitch P2 is configured to allow for myocardial tissue fixation. The helical coil 38 is preferably provided with a tapered distal tip 42 that is configured to penetrate into both the sewing skirt 11, 21 and the heart muscle.

The driver engagement 34 may either be internal or external to the tissue anchor head 32 and tissue anchor head body 36. Where the driver engagement 34 is internal, it is formed as a recess in the tissue anchor head 32 and tissue anchor head body 36. In either the internal or external driver engagement 34 configurations, the tissue anchor head 32 is configured to engage with a driver to apply a torsional force to the helical screw. Where the driver engagement 34 is internal a driver recess, is employed. The driver recess may have any of a large number of known configurations, including, without limitation, slotted, cruciform, internal polygonal, e.g., triangular, quadrilateral, pentagon, hexagon, etc., hexalobular, three-pointed, or tamper resistant, such as, for example, pentalobe. Similarly, where an external driver engagement is provided, the tissue anchor head 32, itself, may have any of a large number of known geometric configurations about the periphery of the tissue anchor head, such as regular or irregular polygonal shapes, e.g., triangular, quadrilateral, pentagonal, hexagonal, etc. Combinations of both internal and external driver engagements are also contemplated and intended by the present disclosure.

As tested in experimental versions and for non-limiting exemplary purposes only, the plurality of tissue anchors 30 may have a cap 32 diameter in the range of about 3 mm to about a helical coil 38 length between about 11 mm and about 15 mm and a coil pitch P1 between about 1.37 mm and about 3.2 mm. Helical coil 38 wire diameter may be in the range of about mm to about 0.686 mm. Those skilled in the art will appreciate that different cap 32 diameters, helical coil 38 lengths, and helical coil pitch P1, as well as the diameter or gauge of the helical coil 38, may be varied to achieve greater or lesser compression pressures between the axial compression ring 102 or axial compression plates 202, the sewing skirt 11, 21 and the tissue to which the apical cuff 10, 20 is coupled. For example, larger cap 32 diameters will allow larger helical coil 38 diameters and different helical coil 38 pitches P1 to be employed to vary the degree of compression applied by cap 32. The cap 32 and/or the driver engagement 34 may also include a visual marker or other indicia that is in axial alignment with the distal tip 42 of the helical coil 38 and aids in visual clocking of the tissue anchor relative to the sewing skirt 11, 21 and the heart muscle.

Figure 6:
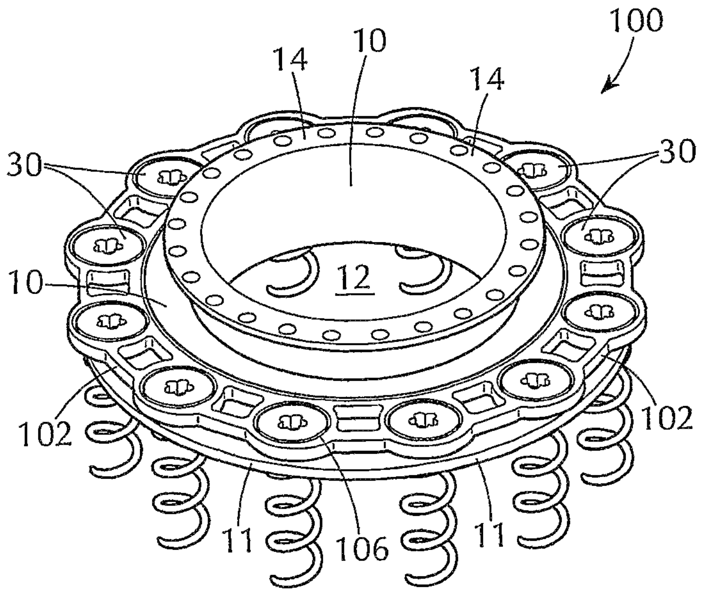
FIG. 6 is a perspective view of the first embodiment of the apical cuff axial compression attachment assembly in its assembled state in accordance with the present disclosure.

FIG. 6 illustrates the assembled configuration of the apical cuff axial compression attachment assembly 100 with the axial compression ring 102 engaged with apical cuff 10 secured with the plurality of tissue anchors 30 passing through the primary openings 106 of the axial compression ring 102 and the sewing skirt 11. The upper flange 14 of the apical cuff 10 is exposed at the upper end of the apical cuff 10 and free of interference by the axial compression ring 102 or tissue anchors 30 to connecting the VAD pump 50 (not shown) to the apical cuff 10. Central opening 12 is unobstructed when the apical cuff axial compression attachment assembly 100 is in its assembled configuration.

Figure 7:
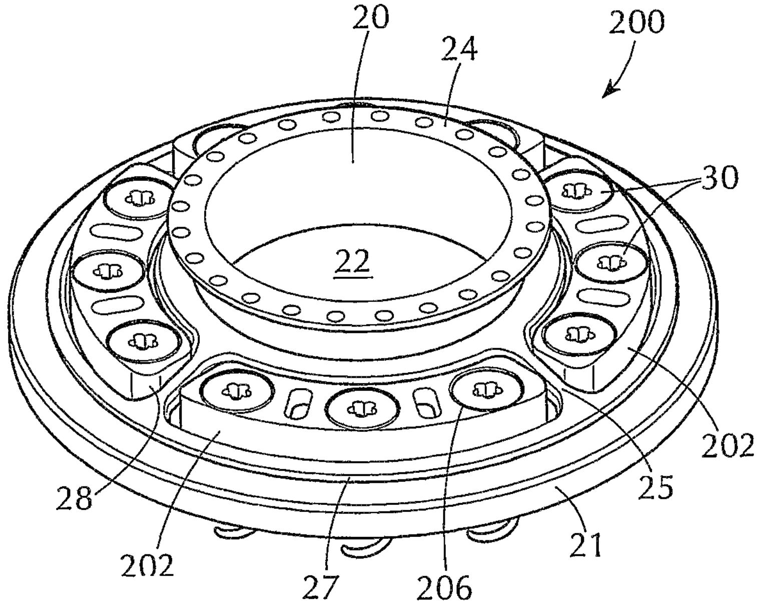
FIG. 7 is a perspective view of the second embodiment of the apical cuff axial compression attachment assembly in its assembled state in accordance with the present disclosure.

FIG. 7 illustrates the assembled configuration of the apical cuff axial compression attachment assembly 200 with the axial compression plates 202 seated within the arcuate openings 28 of the apical cuff 20, and the tissue anchors 30 passing through the primary openings 206 and the sewing skirt 21. Each of the axial compression plates 202 bear against the sewing skirt 21 and are positioned between adjacent pairs of radial arms 25 and the lower flange 26 and outer ring 27. The upper flange 24 of the apical cuff 20 is exposed at the upper end of the apical cuff 20 such that there is no interference from the axial compression plates 202 or tissue anchors 30 with connecting a VAD pump 50 (not shown) to the apical cuff axial compression attachment assembly 20. Central opening 22 is unobstructed when the apical cuff axial compression attachment assembly 200 is in its assembled configuration.

Figure 8:
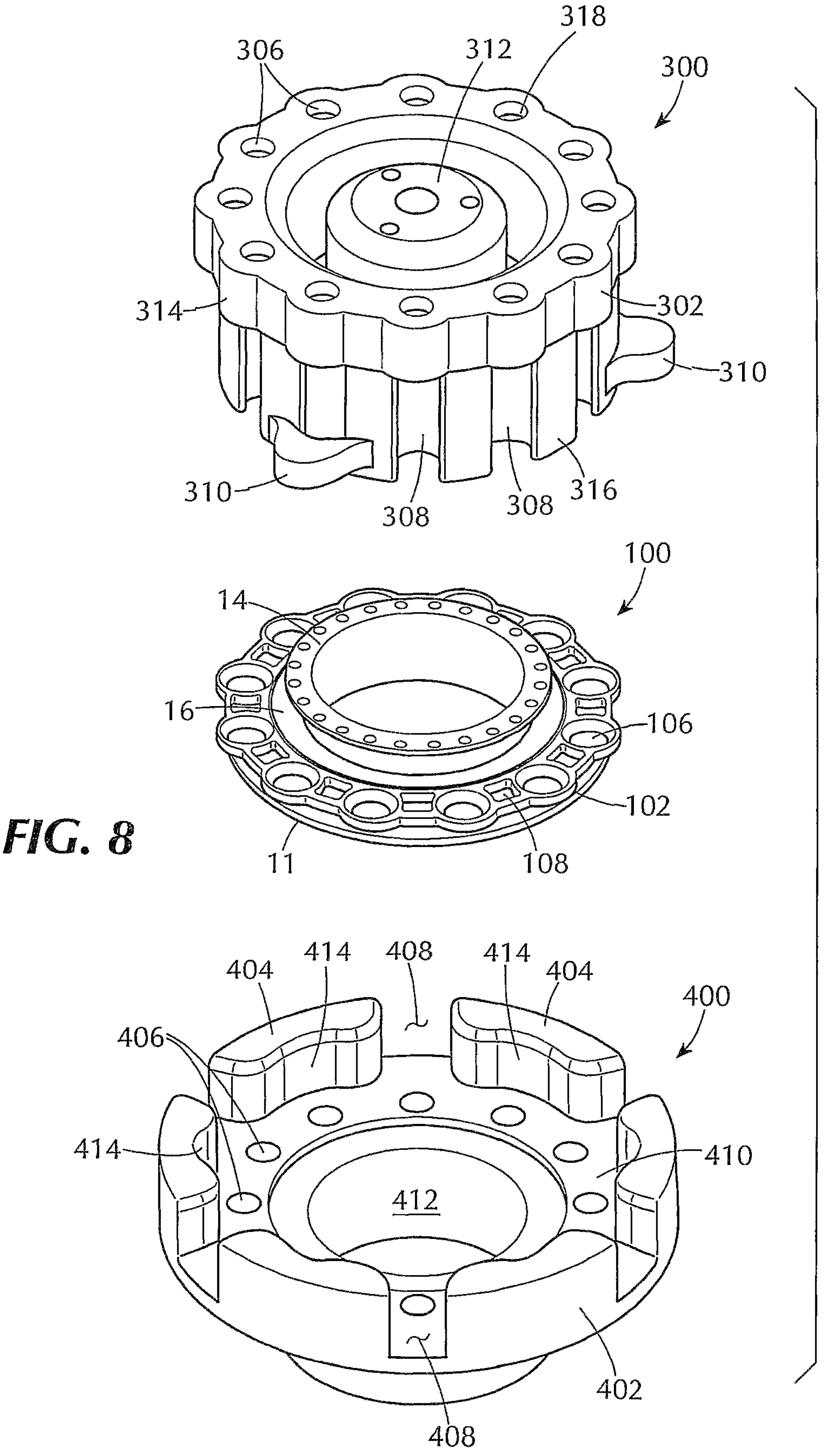
FIG. 8 is an exploded perspective view of a first embodiment of a delivery tool and loading tray together with the assembled apical cuff axial compression attachment assembly in accordance with the first embodiment of the present disclosure.
Figure 13:
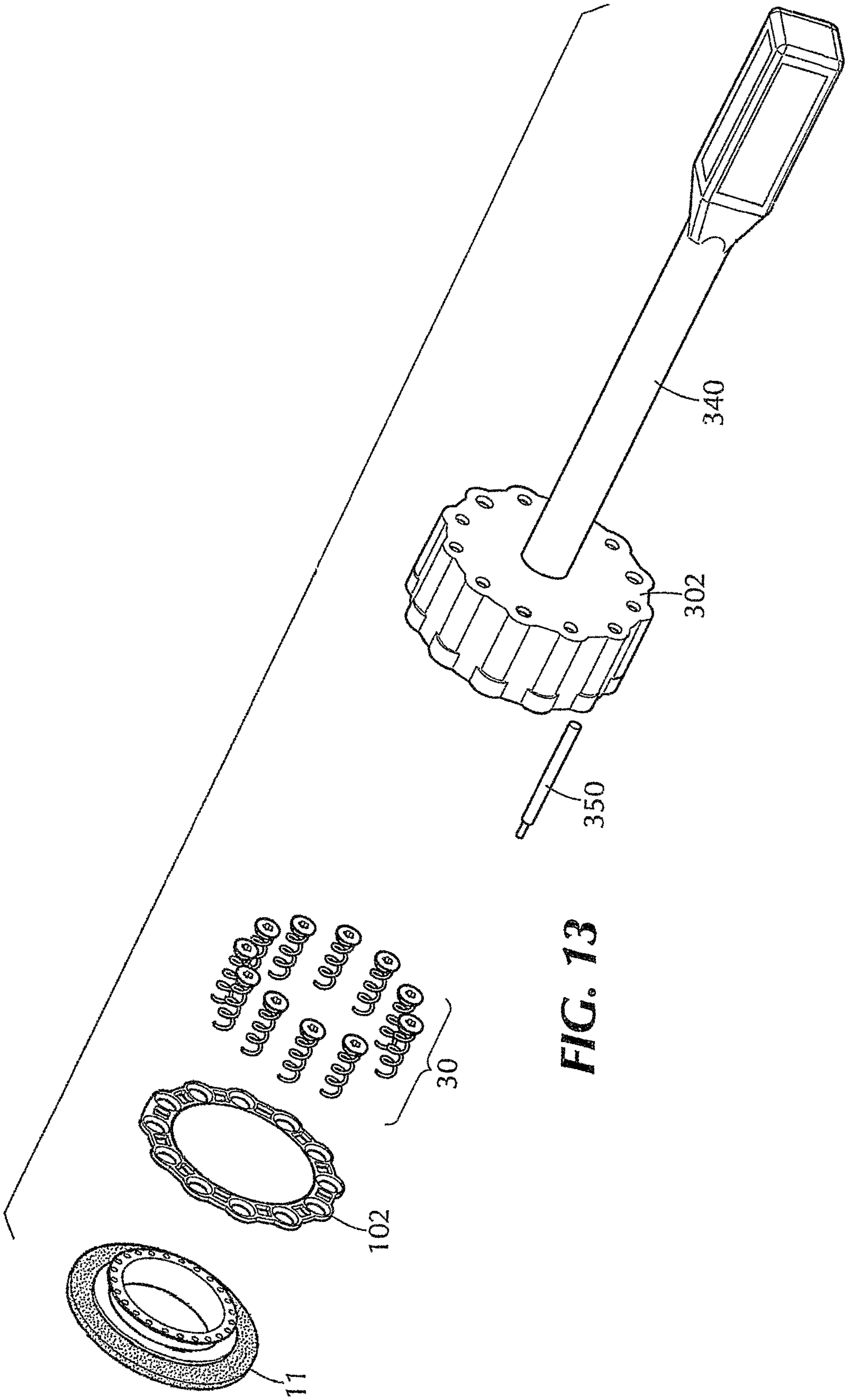
FIG. 13 is an exploded perspective view illustrating the first embodiment of the apical cuff axial compression attachment assembly, the delivery tool and a driver.

To assemble and then deliver the apical cuff axial compression attachment assembly 100 to the heart muscle, the present disclosure provides a delivery tool 300 and a loading tray 400 as illustrated in FIG. 8. The delivery tool 300 serves to align the tissue anchors with the primary openings 106 on axial compression ring 102, guide a driver tool 350 (FIGS. 13, 16, 17) used to drive the tissue anchors 30 through the sewing skirt 11, and then deliver the apical cuff 10 with the coupled apical cuff axial compression attachment assembly 100 to the heart muscle for implantation. Delivery tool 300 consists of a housing 302 having a generally cylindrical configuration with a plurality of recessed channels 308 about the periphery of the housing 302. Each of the plurality of recessed channels 308 is formed in an outer wall surface of the housing 302 and arrayed about the circumference of the housing 302. The housing 302 has an upper portion 314 that projects concentrically outward relative to a lower portion 316. Housing 302 has a length that extends from the upper portion 314 to the lower portion 316 and forms the longitudinal axis of the housing 302. Each of the plurality of channels 308 extends the length of the housing 302 and is open at both the upper portion 314 and lower portion 316 of housing 302. The upper portion 314 of housing 302 may circumferentially enclose each of the plurality of channels 308 and have a plurality of driver openings 306 that each passes through the upper portion 314 of housing 302 and communicates with one of the plurality of channels 308.

With reference to FIG. 8 where an upper portion of each of the plurality of channels 308 is circumferentially enclosed by the upper portion 314 of housing 302, a generally cylindrical bore 318 is created that communicates between the driver openings 306 and the plurality of channels 308. When one or more of the tissue anchors 30 are placed in the plurality of channels 308, the driver engagement 34 of the tissue anchor 30 is co-axially aligned with the driver openings 306 to facilitate engagement of the driver 350 with the tissue anchor 30. Further, bore 318 may be configured to retain the tissue anchor head 32 by a friction fit, interference fit, detents, projections, threads, or the like within the bore 318 such that each tissue anchor 30 is co-axially aligned in the tubular channel 308 and the helical coil 38 is coaxially aligned within each of the plurality of channels 308 in housing 302.

Figure 15:
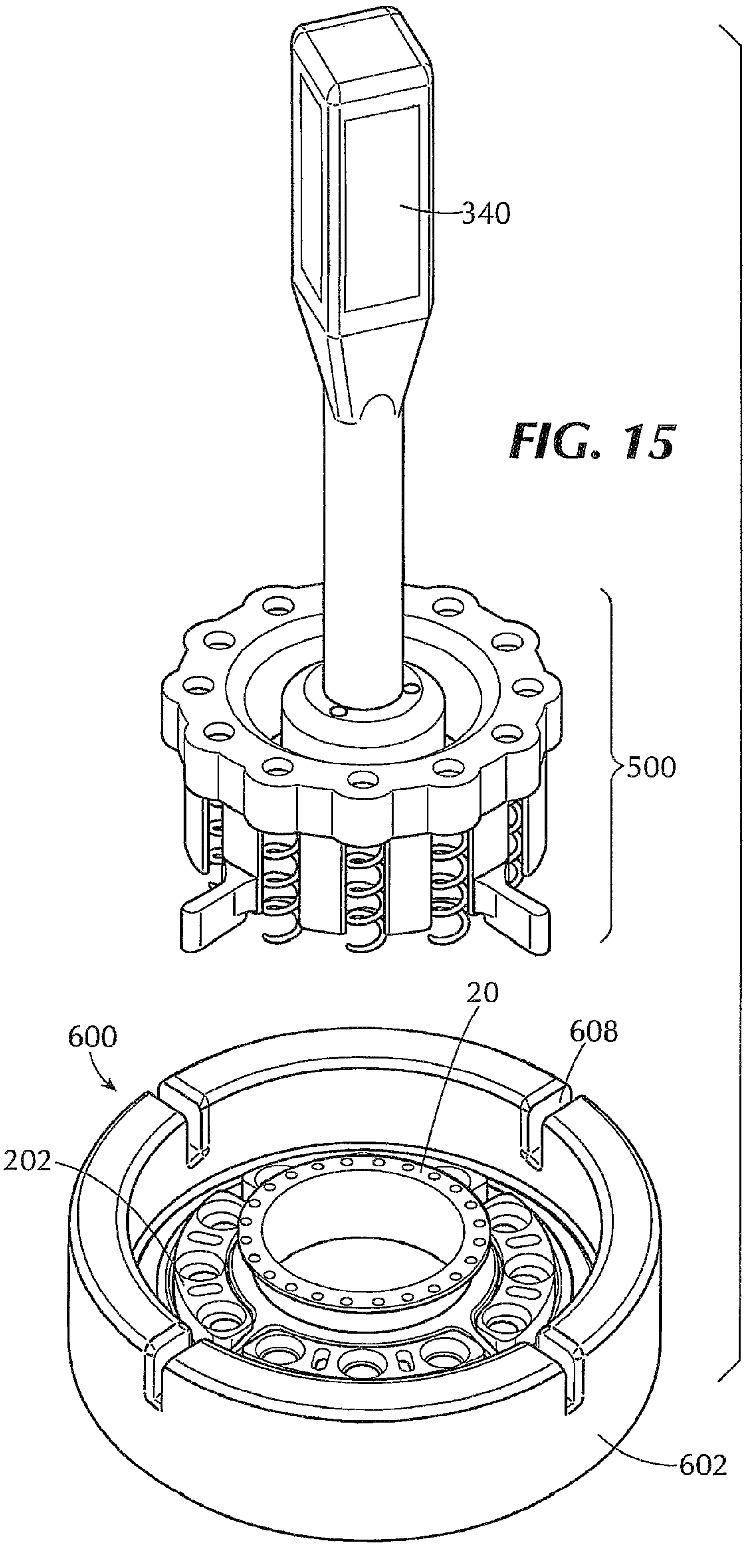
FIG. 15 is an exploded perspective view of the delivery tool, joined with a handle and carrying the helical screws and the loading tray carrying the apical cuff with the axial compression plates engaged with the apical cuff in accordance with the second embodiment of the disclosure.

At least one of a plurality of alignment projections 310 extends radially outward from the lower portion 316 of the housing 302 and serves to align the housing 302 with the loading tray 400. The housing 302 also includes a handle coupling 312 in the upper portion 314 that is accessible from the upper aspect of the upper portion 314. Handle coupling 312 is configured to engage with a handle 340 in FIGS. 13 and 15 in a removable or non-removable manner.

The loading tray 400 is comprised of a loading tray housing 402 that includes a loading tray base 410 having a plurality of tissue anchor openings 406 passing there through and circumferentially arrayed about a circumferential aspect of the loading tray base 410. The plurality of tissue anchor openings 406 are arrayed in alignment with both the plurality of primary openings 106 in axial compression ring 102 and with the plurality of channels 308 in the delivery tool housing 302. Loading tray housing 402 also includes a plurality of abutment projections 404 which extend upward about the perimeter of the loading tray housing 402. A plurality of alignment openings 408 are positioned between adjacent pairs of the plurality of abutment projections 404 and are spaced apart in alignment with the plurality of alignment projections 310 of the delivery tool housing 302.

Where the axial compression ring 102 is provided with a plurality of radial projections 110 about the circumference of the axial compression ring 102, each of the abutment projections 404 may also have a recess 414 on an inner wall surface of at least some of the abutment projections 404. Recess 414 may be positioned at a center point of the inner wall surface of the abutment projections 404 and will preferably have a length corresponding to the height of the abutment projections 404 from the loading tray base 410. Further, recess 414 may have a shape corresponding to a shape of the radial projection 110 on the axial compression ring 102 such that the recess 414 is configured to receive a radial projection 110 therein and seat the axial compression ring 102 within the abutment projections 404.

Turning now to FIGS. 9-12 and FIGS. 14-17, for the apical cuff axial compression attachment assembly 200 there is provided a delivery tool 500 and a loading tray 600. To assemble and then deliver the apical cuff axial compression attachment assembly 200 to the heart muscle, the present disclosure provides the delivery tool 500 and the loading tray 600. The delivery tool 500 also serves to align the tissue anchors 30 with the primary openings 206 in the plurality of axial compression plates 202, guide the driver tool 350 (FIGS. 13, 16) used to drive the tissue anchors 30 through the sewing skirt 21, and then deliver the apical cuff 20 with the coupled apical cuff axial compression attachment assembly 200 to the heart muscle for implantation. Delivery tool 500 also consists of a housing 502 having a generally cylindrical configuration with a plurality of recessed channels 508 about the periphery of the housing 502. Like with delivery tool 300, each of the plurality of recessed channels 508 is formed in an outer wall surface of the housing 502 and arrayed about its circumference. The housing 502 has an upper portion 514 that projects concentrically outward relative to a lower portion 516. Housing 502, like housing 302, has a length that extends from the upper portion 514 to the lower portion 516 and forms the longitudinal axis of the housing 502. Each of the plurality of channels 508 extend the length of the housing 502 and are open at both the upper portion 514 and lower portion 516 of housing 502. The upper portion 514 of housing 502 may circumferentially enclose each of the plurality of channels 508 and have a plurality of driver openings 506 that each pass through the upper portion 514 of housing 502 and communicate with one of the plurality of channels 508.

Figure 9:
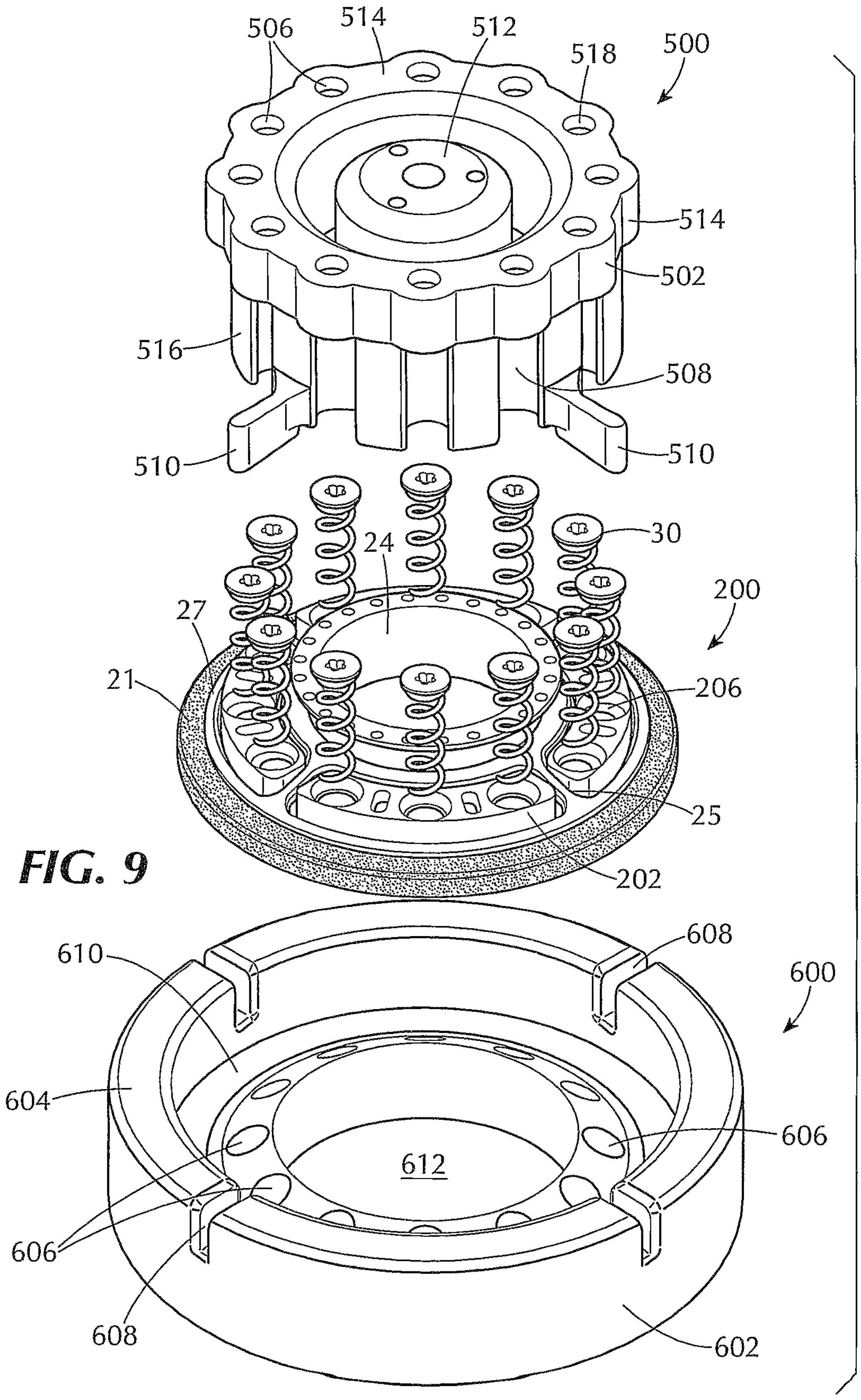
FIG. 9 is an exploded perspective view of a second embodiment of a delivery tool and loading tray together with an assembled apical cuff axial compression attachment assembly with affixation members in accordance with the second embodiment of the present disclosure.
Figure 10:
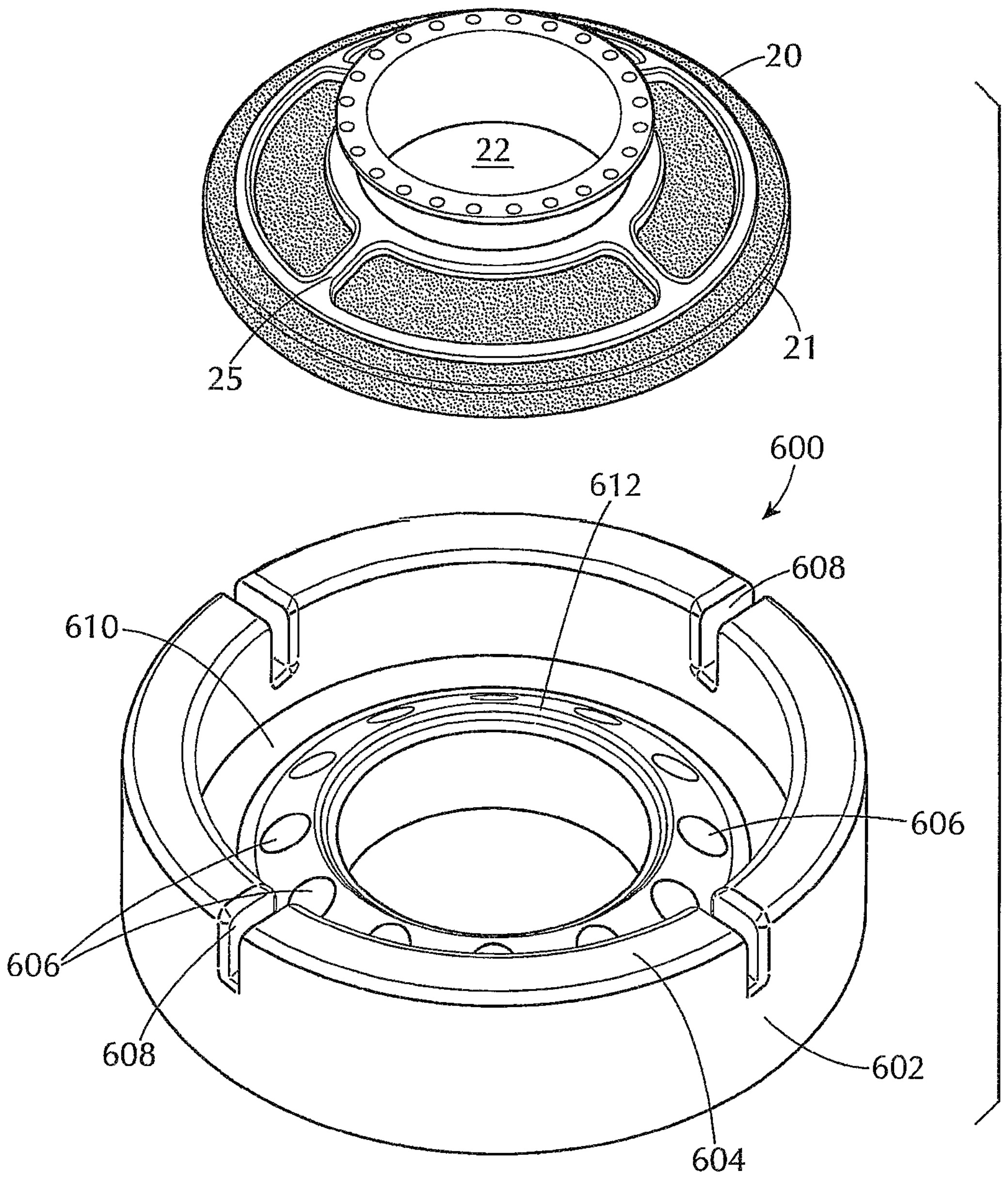
FIG. 10 is an exploded perspective view of an apical cuff and loading tray in accordance with the second embodiment of the present disclosure.
Figure 11A:
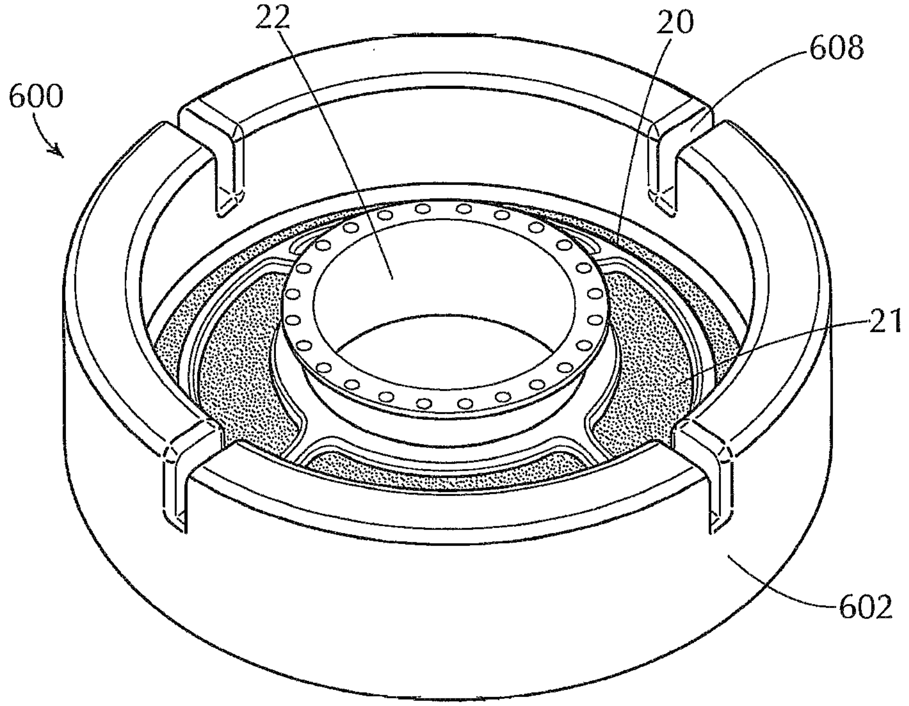
FIG. 11A is a perspective view of an apical cuff engaged with the loading tray in accordance with the second embodiment of the present disclosure.
Figure 11B:
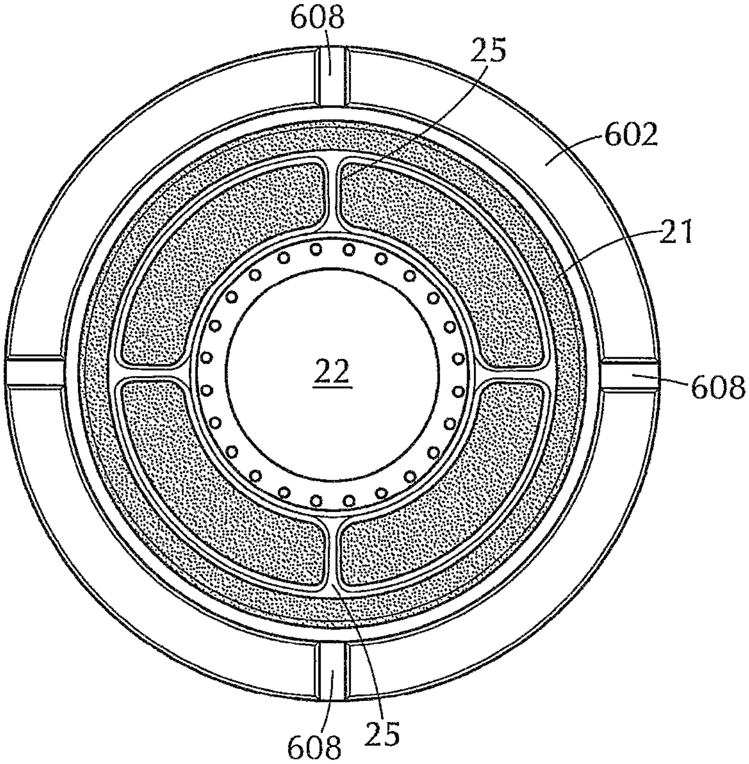
FIG. 11B is a top elevational view of FIG. 11A.
Figure 12:
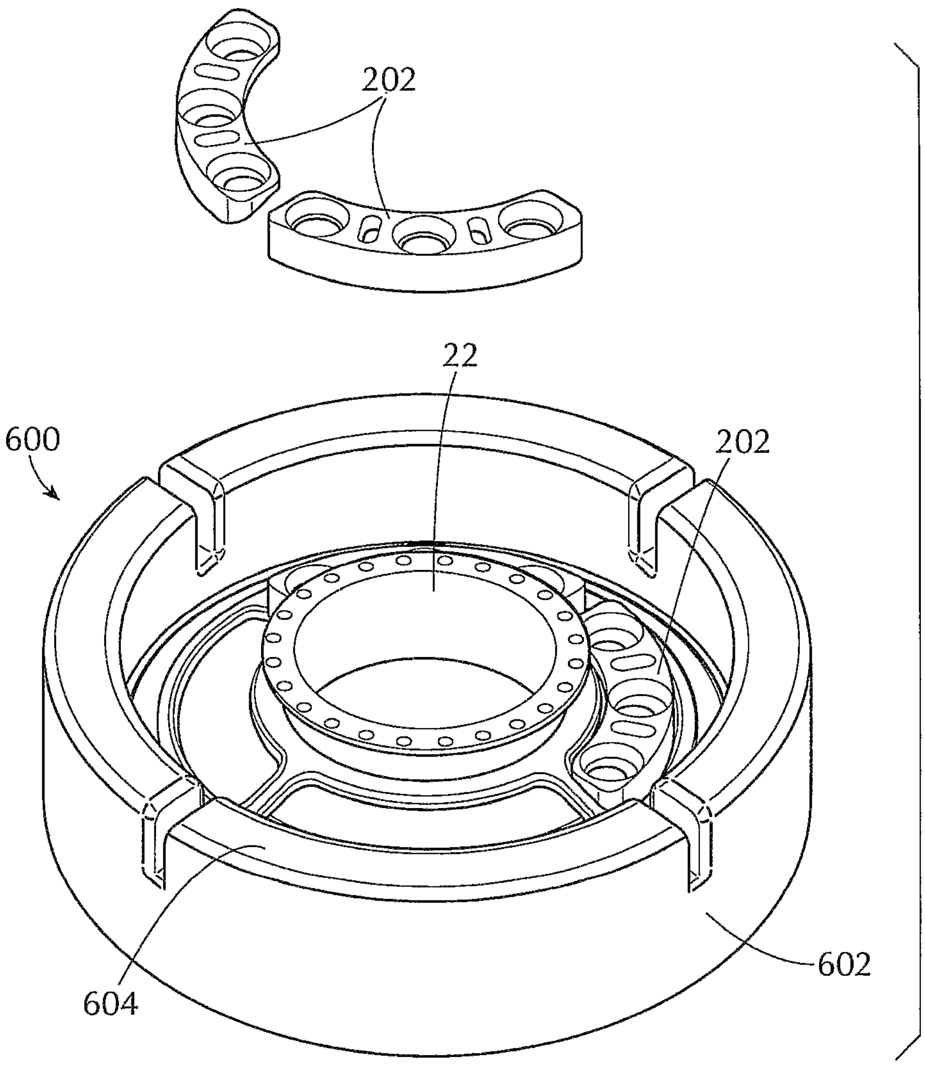
FIG. 12 is an exploded perspective view illustrating assembly of axial compression plates with the apical cuff in the loading tray in accordance with the second embodiment of the present disclosure.
Figure 14:
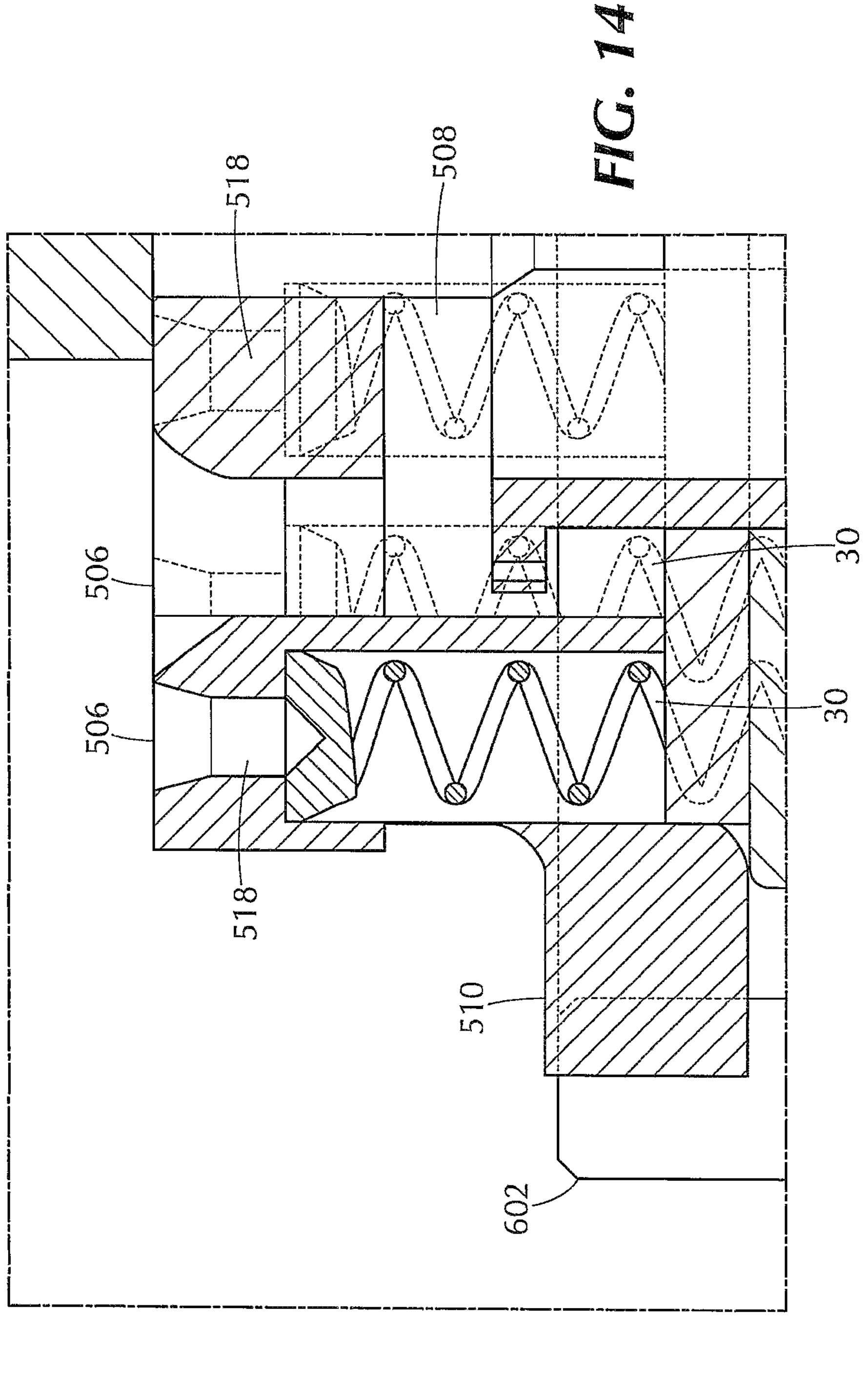
FIG. 14 is a fragmentary side elevational partial cross-sectional view showing the delivery tool carrying the helical screws in accordance with the second embodiment of the disclosure.
Figure 16:
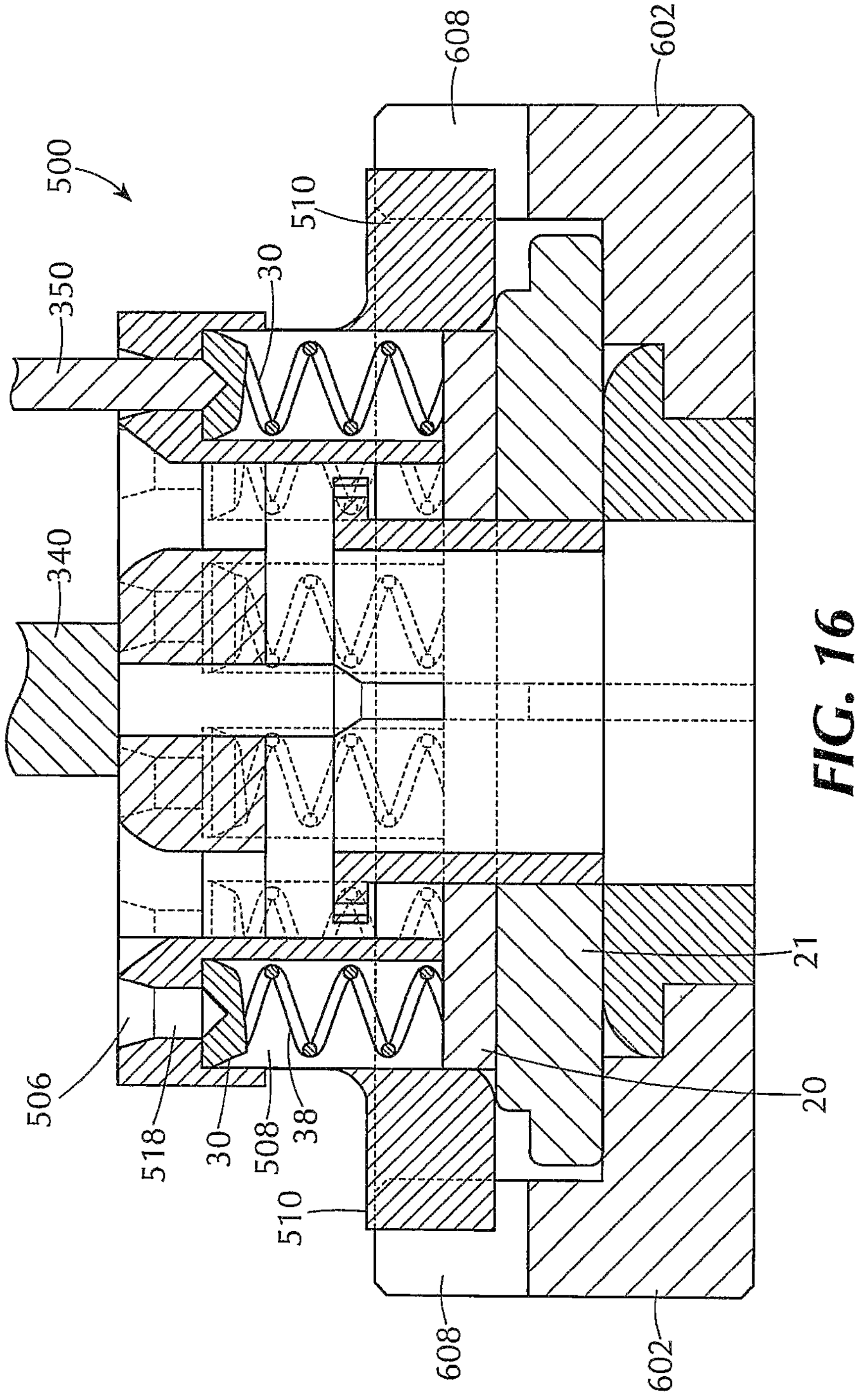
FIG. 16 is a side elevational partial cross-sectional view of the assembled delivery tool, helical screws, apical cuff and loading tray, together with the handle and driver in accordance with the second embodiment of the disclosure.

With reference to FIGS. 9, 14 and 16, where an upper portion of each of the plurality of channels 508 is circumferentially enclosed by the upper portion 514 of housing 502, a plurality of bores 518 each communicates between a corresponding driver opening 506 and a corresponding channel 508. When one or more of the tissue anchors 30 are placed in the plurality of channels 508, the driver engagement 34 of the tissue anchor 30 is co-axially aligned with the driver openings 506 to facilitate engagement of the driver 350 with the tissue anchor 30. Channels 508 may be configured to retain the tissue anchor head 32 by a friction fit, interference fit, detents, projections, threads, or the like within the bore 518 such that each tissue anchor 30 is co-axially aligned with bore 518 and the helical coil 38 is coaxially aligned within each of the plurality of channels 508.

At least one of a plurality of alignment projections 510 extend radially outward from the lower portion 516 of the housing 502 and serve to align the housing 502 with the loading tray 600. The housing 502 also includes a handle coupling 512 in the upper portion 514 that is accessible from the upper aspect of the upper portion 514. Handle coupling 512 is configured to engage with a handle 340 in FIGS. 13 and 15 in a removable or non-removable manner.

With reference to FIGS. 9-12, 15, and 17 loading tray 600 is comprised of a loading tray housing 602 that includes a loading tray base 610 having a plurality of tissue anchor openings 606 passing there through and circumferentially arrayed about a circumferential aspect of the loading tray base 610. Loading tray base 610 may have a slope or radiused curvature extending from the central opening 612 radially outward toward the perimeter of the loading tray base 610 that matches or approximates the slope or curvature of the radial arms 25 of the apical cuff 20. Where the loading tray base 610 has a sloped portion about the periphery of the central opening 612, the plurality of tissue anchor openings 606 may pass through the sloped portion of the loading tray base 610. The plurality of tissue anchor openings 606 are arrayed in axial alignment with both the plurality of primary openings 206 in the plurality of axial compression plates 202 and with the plurality of channels 508 in the delivery tool housing 502. Loading tray housing 602 also has a circumferential wall 604 that projects upwardly about the circumference of the loading tray housing 602. A plurality of alignment openings 608 pass through the circumferential wall 604, such as vertical slots 608 in the circumferential wall 604, that are spaced apart from each other about the circumference of the circumferential wall 604. The alignment openings 608 are positioned to align with and engage the plurality of alignment projections 510 of the delivery tool housing 502, thereby co-axially aligning the driver openings 506, the bores 518, the channels 508, the tissue anchors 30, the primary openings 206 in the axial compression plates 202, with the plurality of openings 606 in the loading tray base 610.

Figure 26:
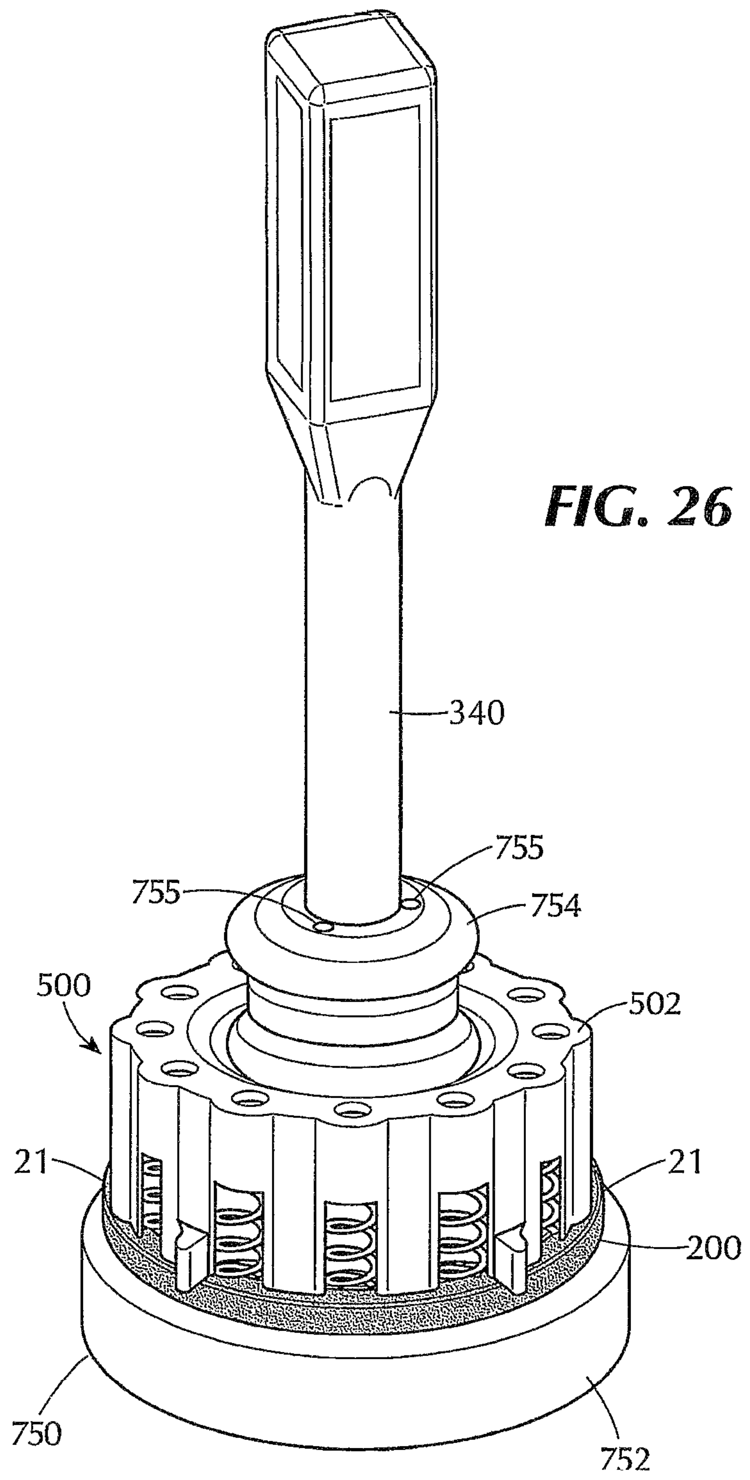
FIG. 26 is a perspective view of an alternative embodiment of the apical cuff delivery tool, loading tray and apical cuff axial compression attachment assembly in accordance with the present invention.

An alternative embodiment of the loading tray 750 is shown in FIGS. 26-31. FIG. 26 illustrates a perspective view of an assembled delivery tool 500, an apical cuff axial compression attachment assembly 200, and a loading tray 750. Loading tray 750 is similar to loading tray 600, except that the circumferential wall 604 and vertical slots 608 are not present. Like loading tray 600, loading tray 750 has a loading tray base 610 having a sloped or curved section extending from the central opening 612, and a plurality of tissue anchor openings 606 passing axially through the sloped or curved section of the loading tray base. The central opening 612 is also present, however, a support structure 760 subtends the central opening 612 and carries at least two boss member projections 772 that project axially upward from the support structure 760. The at least two boss member projections 772 engage with corresponding mating recesses (not shown) in a lower surface of the delivery tool 500 and assist in aligning the delivery tool 500 with the loading tray 750 such that the plurality of openings 606 in the loading tray 750 are in axial alignment with the plurality of channels 508 and the tissue anchors 30 in the delivery tool 500.

Figure 27:
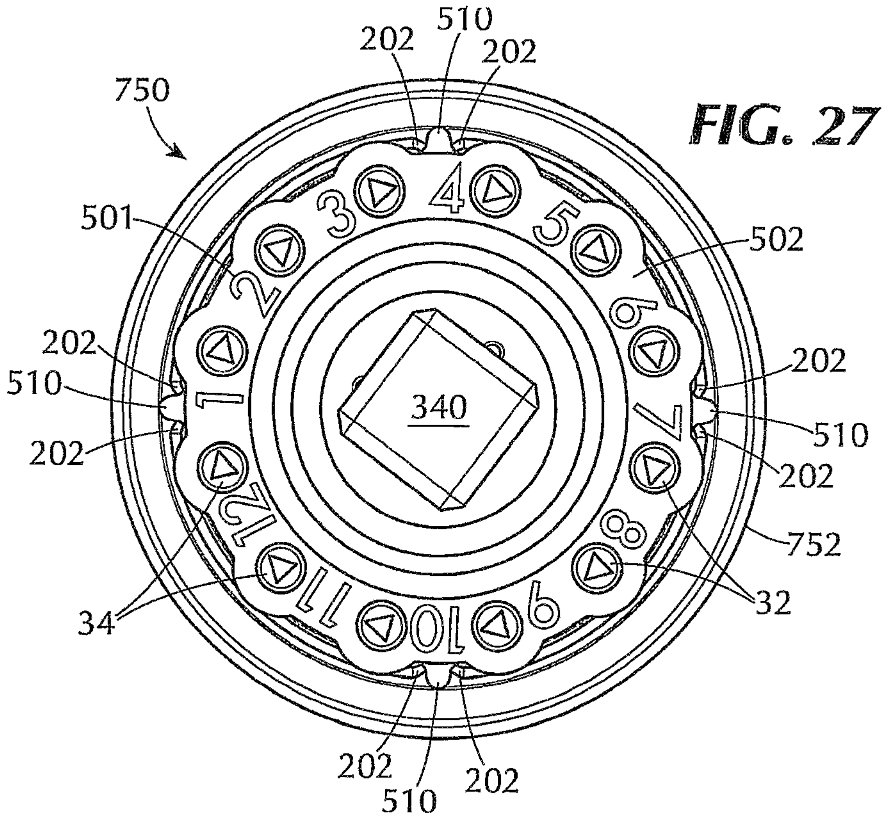
FIG. 27 is a top plan view of the alternative embodiment of the apical cuff delivery tool, loading tray and apical cuff axial compression attachment assembly in accordance with the present invention.

FIG. 27 is a top plan view of FIG. 26 and illustrates the plurality of tissue anchors and associated driver engagements 34 retained within the seating channels of the delivery tool housing 502. In this exemplary illustration, numerical positional indicia 501 are associated with the top of the delivery tool housing 502 adjacent to each driver opening 506.

Figure 28:
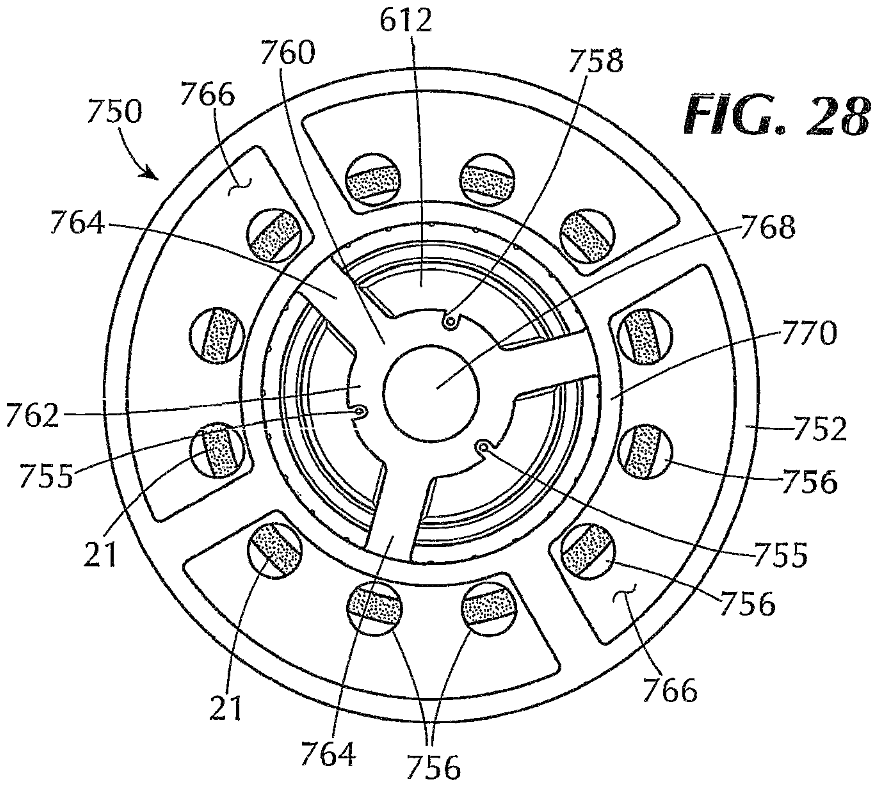
FIG. 28 is a bottom plan view of the alternative embodiment of the apical cuff delivery tool, loading tray and apical cuff axial compression attachment assembly in accordance with the present invention.

FIG. 28 is a bottom plan view of FIG. 26 and illustrates the loading tray 750 and its plurality of openings 756 through which the sewing skirt 21 is visible. The support structure 760 is also depicted in FIG. 28.

The support structure 760 may further include a plurality of recesses 758 on lateral surfaces of the support structure 760. The plurality of recesses 758 are configured to accommodate axial movement of pins 755 to pass axially along each of the plurality of recesses 758. As is illustrated in FIG. 26, handle 340 may include an annular member 754 that carries pins 755 and is either in a fixed position or is reciprocally coupled to the handle 340 such that the annular member 754 moves axially along the handle 340. The annular member 754 carries the plurality of pins 755 that project axially downward from a lower surface of the annular member 754 and are configured to pass through the central opening 204 of the apical cuff 20 to engage the heart tissue during the delivery procedure to assist the surgeon in positioning the apical cuff connected to the apical cuff axial compression attachment assembly 200, on the heart.

An annular opening 768 may be provided in the support structure 760 and centrally positioned relative to the loading tray 750. This annular opening 768 may be configured to receive a securing device, such as a screw, clamp or other device configured to secure the loading tray 750 and the apical cuff 200 to the delivery tool 500 in an assembled state, such as is illustrated in FIG. 26. The annular opening 768 may pass through a central ring member 762 which is carried on a plurality of radial support arms 764 that extend radially from the central ring member 762 to a circular boss 770 that projects from the loading tray base 766. The circular boss 770 is then connected to the loading tray housing 752 by a plurality of outer support radial arms 776. The support structure 760 and its associated central ring member 762, radial support arms 764, circular boss 770, outer support radial arms 776, and the loading tray housing 752 may be molded or formed as a single unitary piece or may be plural pieces joined to one another.

Figure 29:
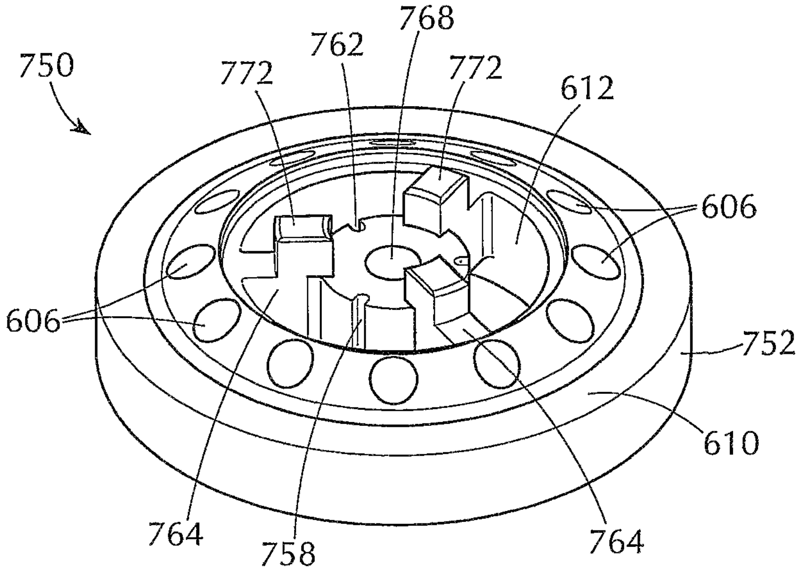
FIG. 29 is a perspective view of an alternative embodiment of a loading tray in accordance with the present invention.
Figure 30:
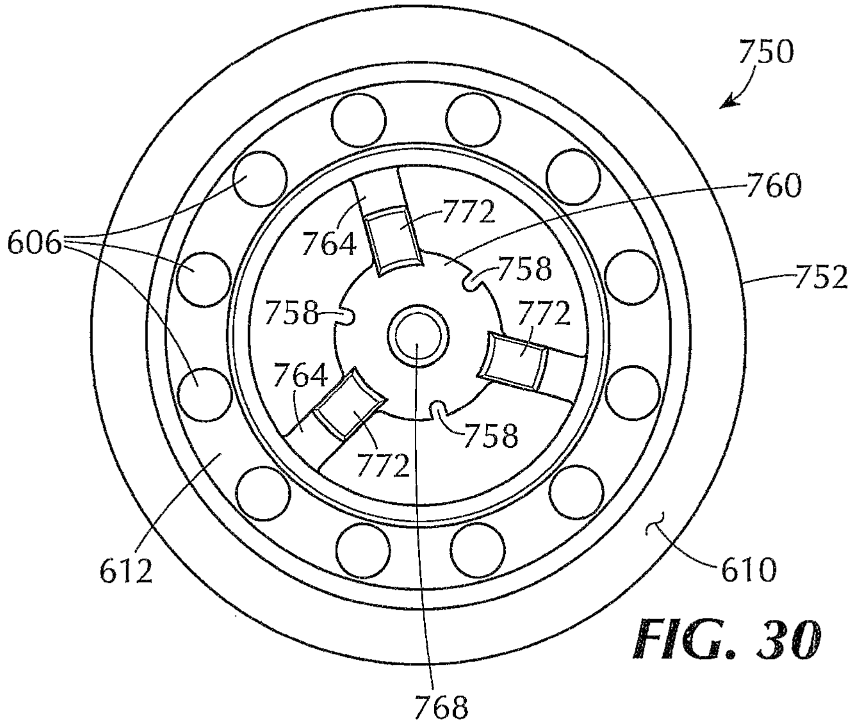
FIG. 30 is a top plan view of the alternative embodiment of the loading tray in accordance with the present invention.
Figure 31:
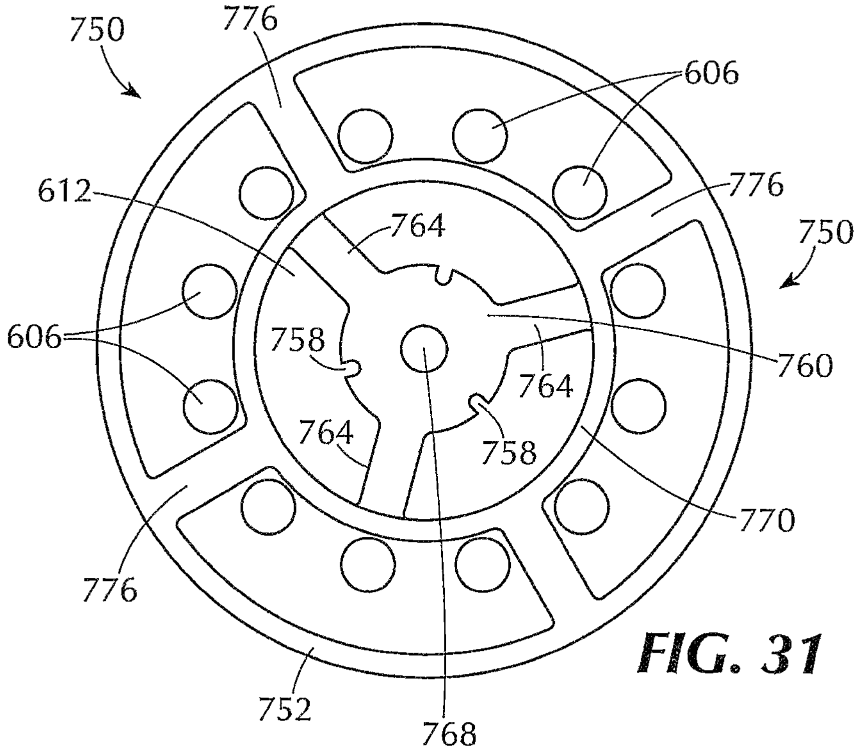
FIG. 31 is a bottom plan view of the alternative embodiment of the loading tray in accordance with the present invention.

FIGS. 29-31 depict only the loading tray 750 and its associated structures, described above, in perspective, top view and bottom view, respectively, without the associated apical cuff axial compression attachment assembly 200 or the delivery tool 500 joined thereto.

Figure 17:
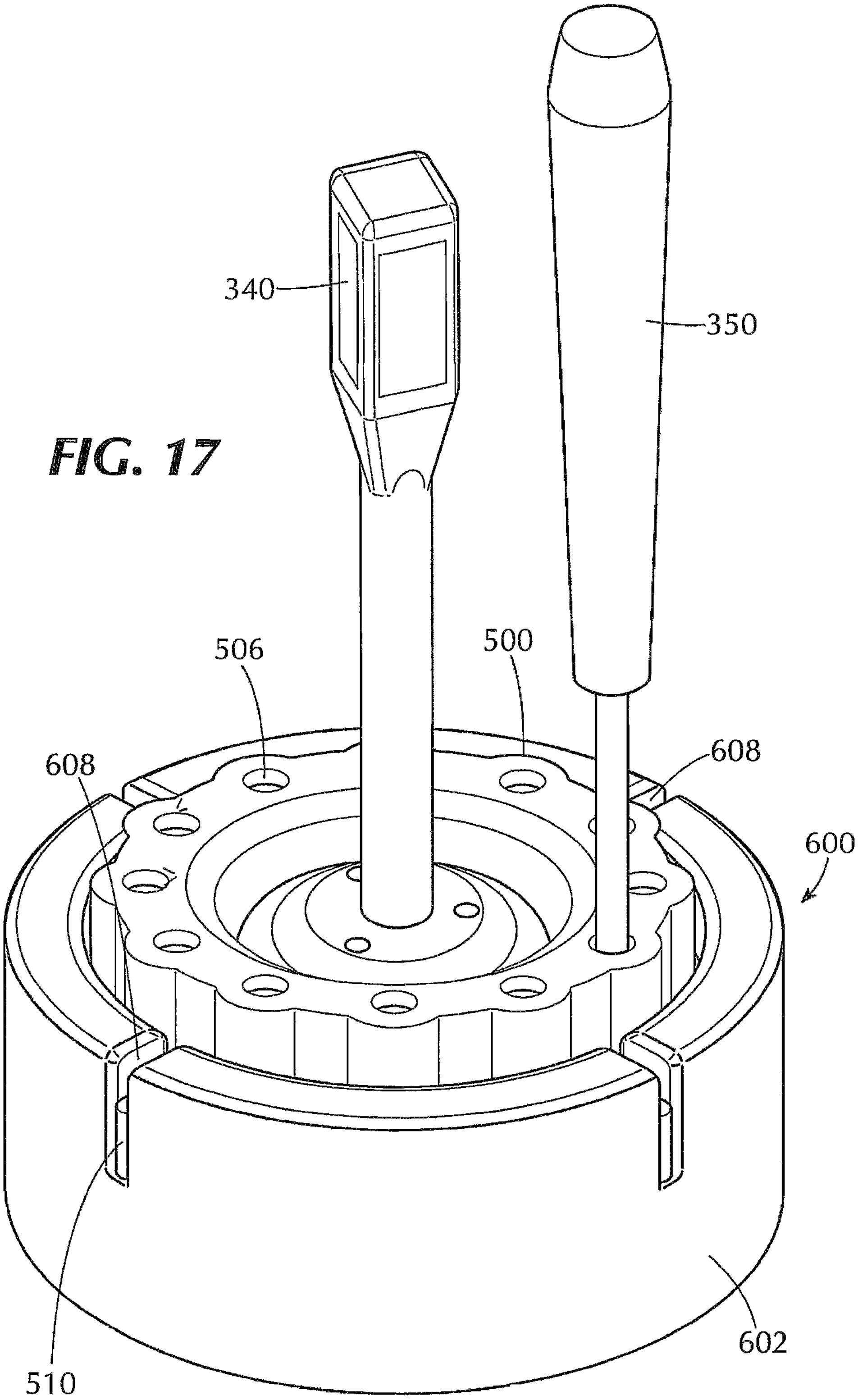
FIG. 17 is a perspective view of FIG. 16.
Figure 19:
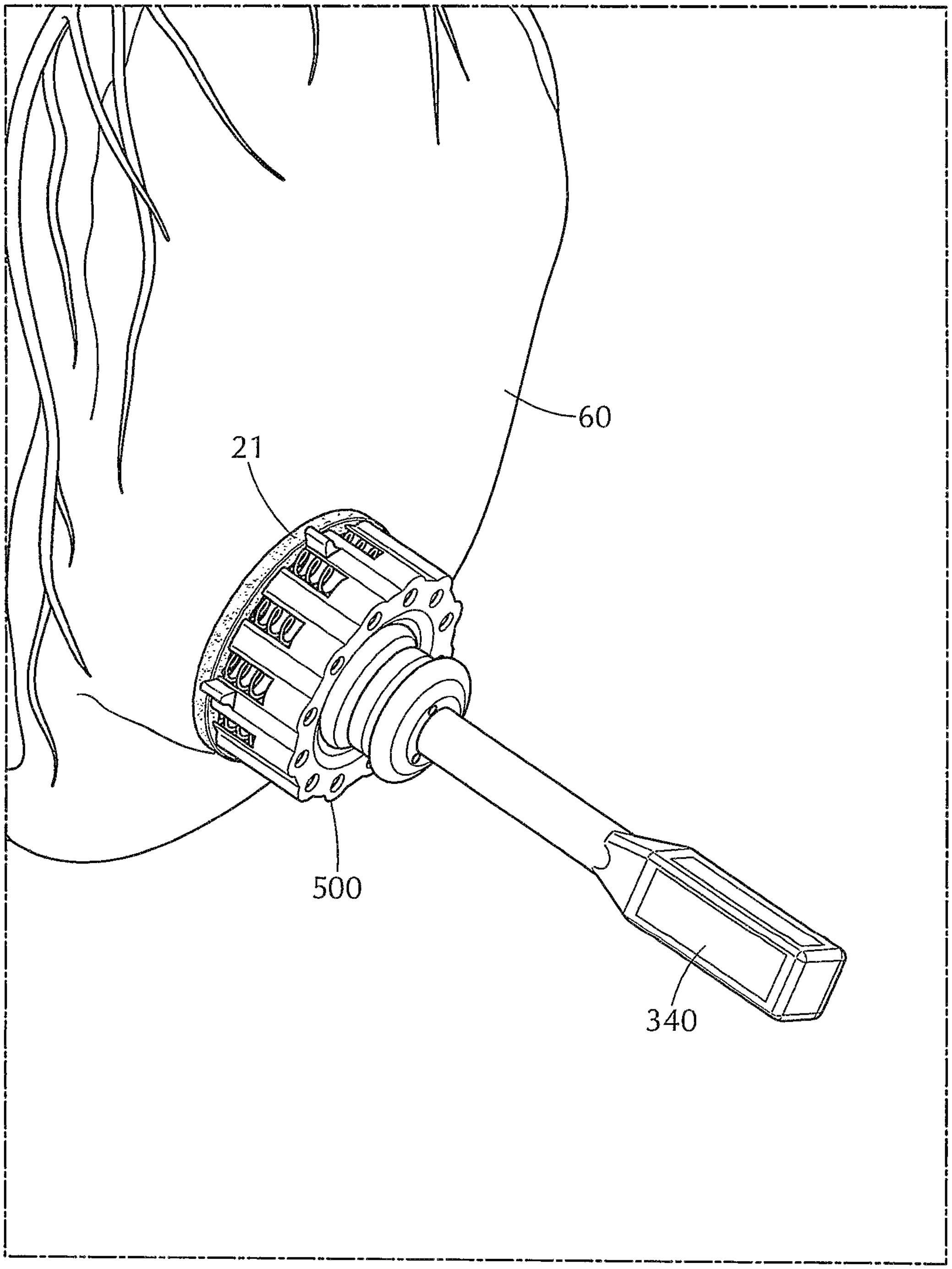
FIG. 19 is a perspective view of the apical cuff axial compression attachment assembly and delivery tool, and apical cuff placed on a heart in preparation for fixation to the heart.

As is illustrated in FIG. 17, in operation, an apical cuff 20 and compression plates 202 are loaded into delivery tool 500 and positioned in loading tray 600 using handle 340 to engage the delivery tool 500 with the loading tray 600. The driver 350 is then passed through the driver openings 506 and engaged with the driver engagement 34 in each of the plurality of tissue anchors 30 retained within tissue anchor retention channels 508. Torsional rotation of the driver 350 on each of the plurality of tissue anchors 30 drives the distal tip 42 of the helical coil 38 into the sewing skirt 21 and, thereby, engages the apical cuff 20 with the plurality of tissue anchors 30 and the delivery tool 500. Once each of the plurality of tissue anchors 30 is engaged with the sewing skirt 21 of the apical cuff 20, the handle is used to disengage the delivery tool 500, with the now coupled apical cuff 20, from the loading tray 600. At this point, the delivery tool 500 coupled with the apical cuff 20 and apical cuff axial compression attachment assembly 200 is positioned against the heart muscle 60 as illustrated in FIG. 19.

Figure 20:
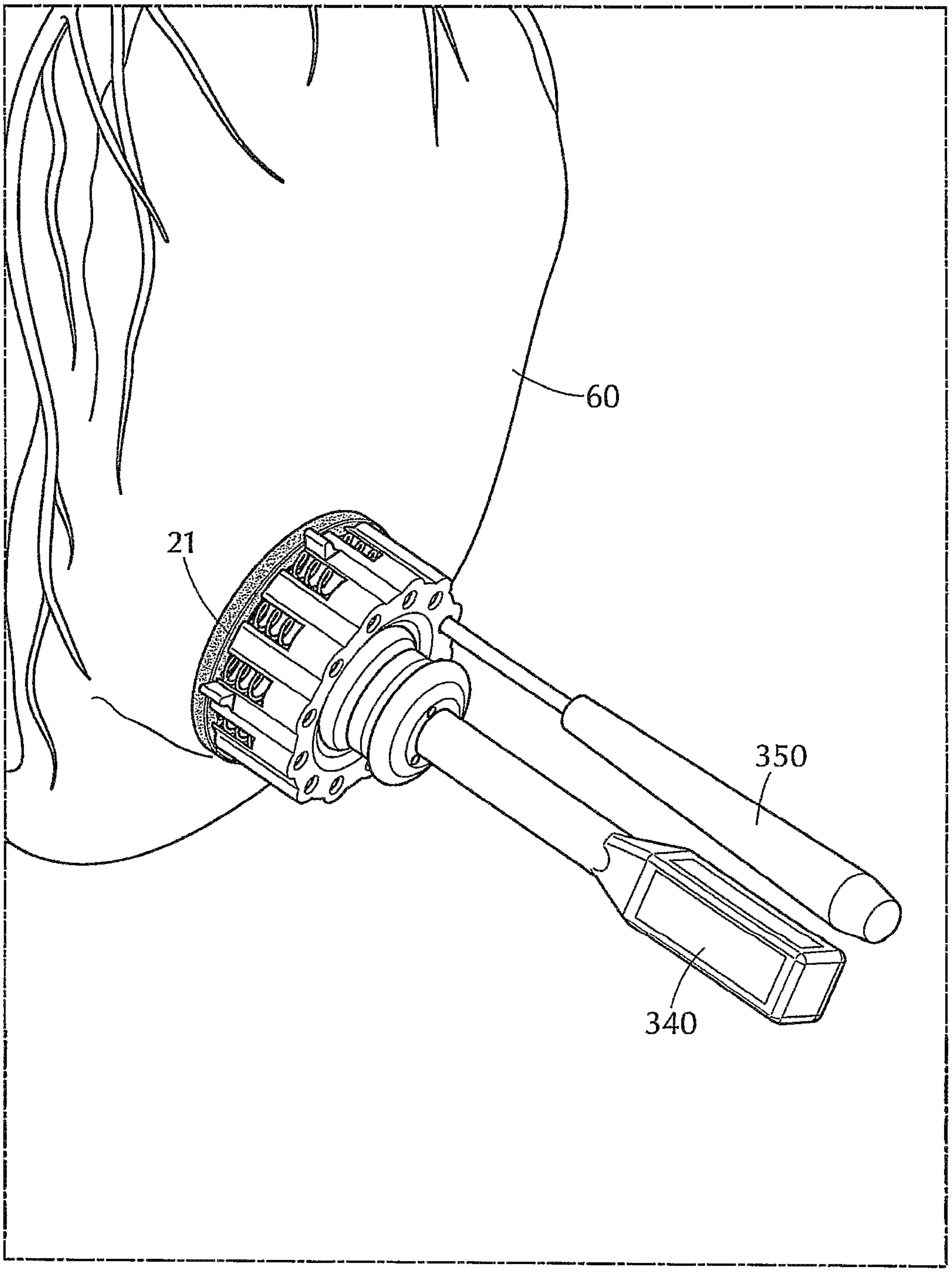
FIG. 20 is a perspective view of FIG. 19 showing the driver in engagement with the helical screws through the delivery tool in accordance with the second embodiment of the disclosure.
Figure 21:
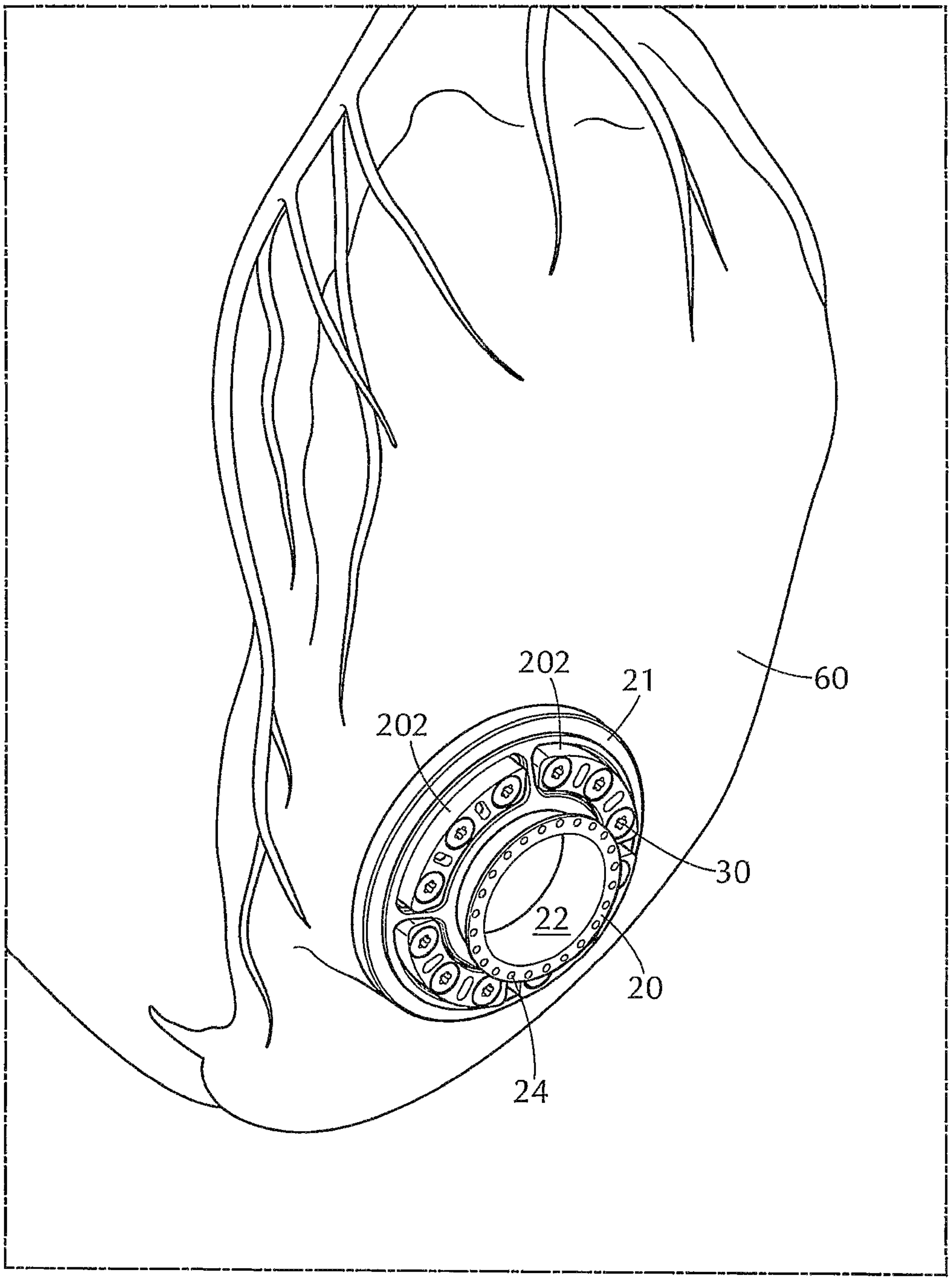
FIG. 21 is a perspective view of an apical cuff, the axial compression plates and the helical screws joined to a heart in accordance with a second embodiment of the present disclosure.

Once the delivery tool 500 and the coupled apical cuff 20 are placed against the heart muscle 60, the driver 350 is again engaged with the driver engagement 34 of each of the plurality of tissue anchors 30 and each of the plurality of tissue anchors 30 is driven into the heart muscle 60 as illustrated in FIGS. 20 and 21. Once each of the plurality of tissue anchors 30 is set within the heart muscle 60, and the torsional force applied achieves a hemostatic seal between the heart muscle 60 and the sewing skirt 21, the delivery tool 500 and driver may be removed, as illustrated in FIG. 21.

Figure 18:
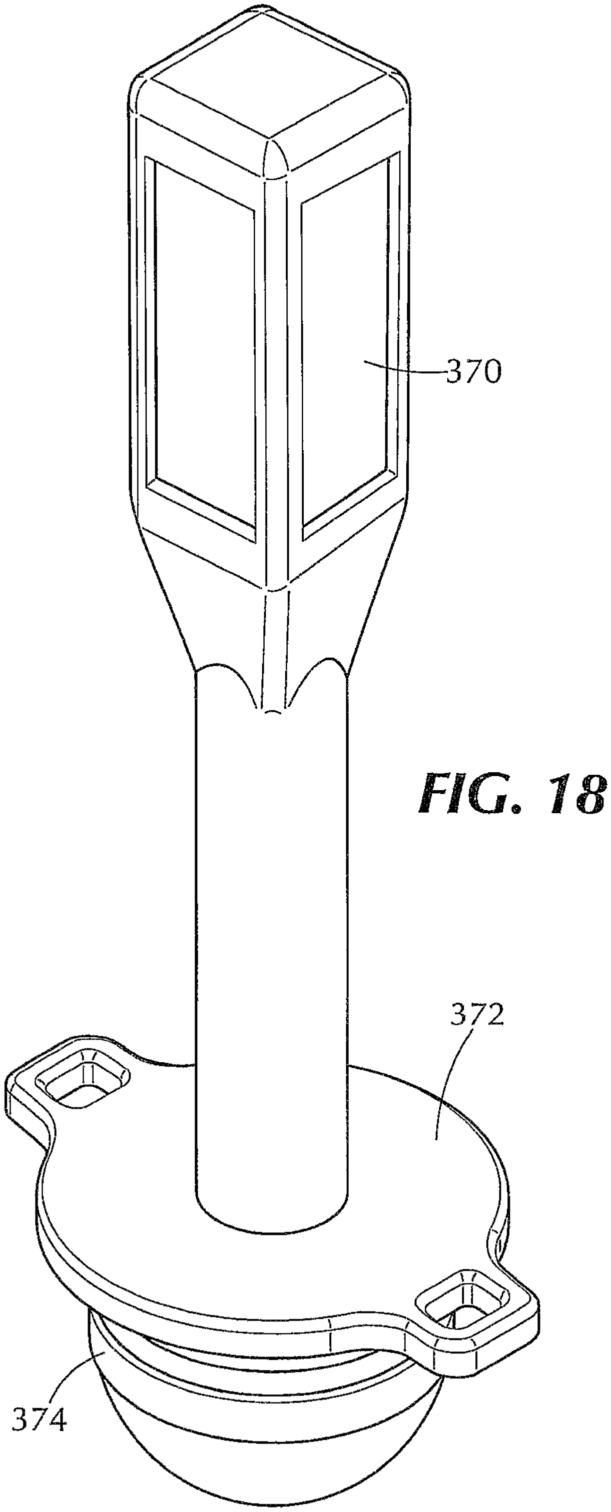
FIG. 18 is a perspective view of an apical cuff central bore plug tool employed experimentally to test hemostasis during bovine heart experiments employing the first and second embodiments of the present disclosure.
Figure 22:
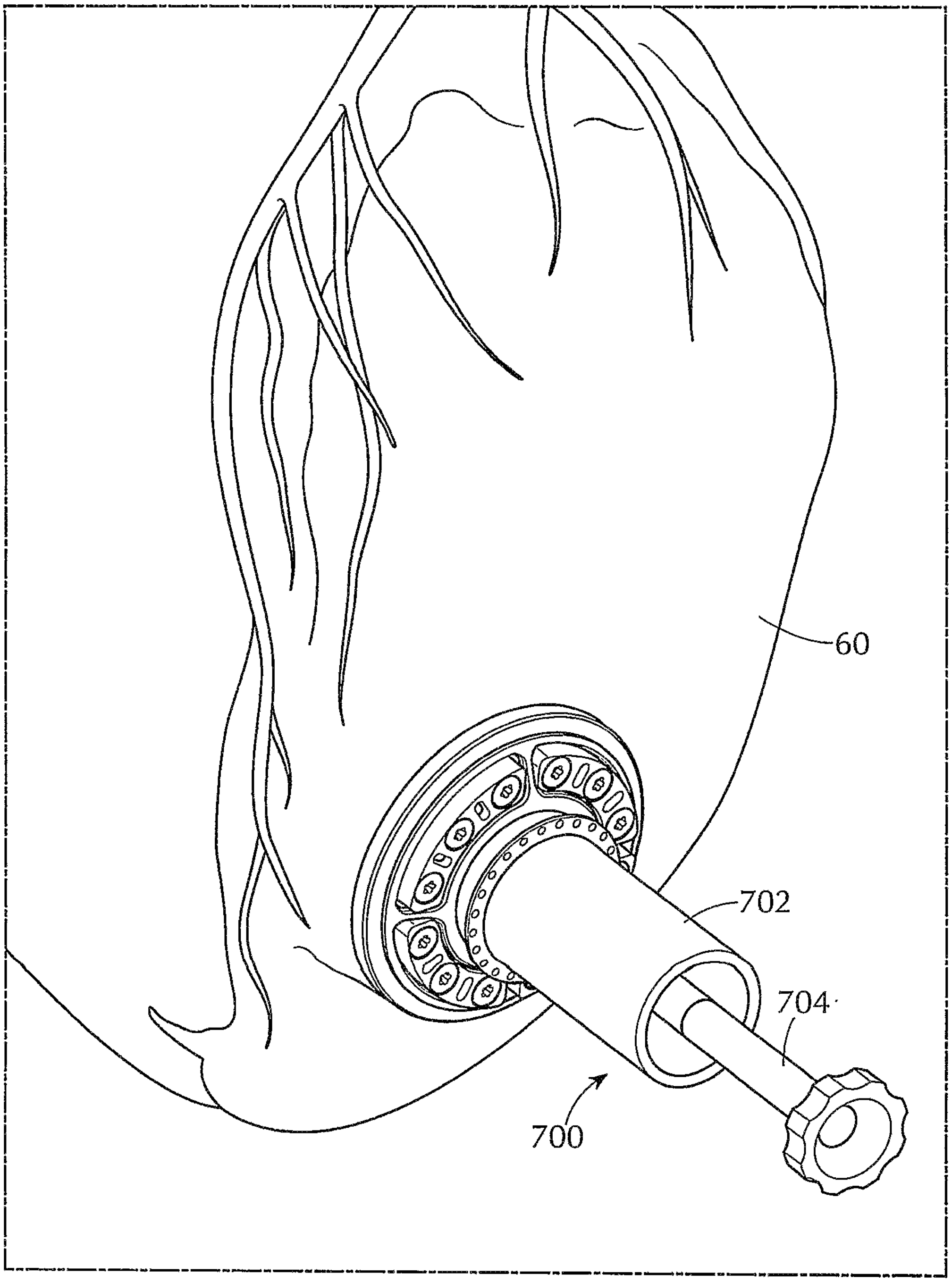
FIG. 22 is a perspective view of a coring tool, employed experimentally, placed within the central opening of the apical cuff for coring the heart muscle in accordance with either the first or second embodiments of the disclosure.

As illustrated in FIG. 22, the heart muscle 60 is cored to open the heart ventricle and the VAD pump 50 is mechanically coupled to the apical cuff 20. A coring tool 700 is placed within the central opening 22 of the apical cuff 20 such that a circular coring blade 702 is concentrically positioned within the central opening 22, and a coring handle 704 is operated to cut a circular section of the heart muscle 60. Once the heart muscle is cored, the coring tool is removed along with the heart muscle core. In an experimental model, a plug tool 370, such as that illustrated in FIG. 18, is coupled to the central opening 22 of the apical cuff 20 to prevent bleeding through the cored opening in the heart muscle 60 and assess hemostasis. The plug tool 370 may have a plug member 374 that partially or entirely occludes the cored opening in the heart muscle 60. Plug member 374 is carried on a plug base 372 which, in turn, is carried on a handle that allows the user to manipulate the plug tool 370.

In clinical use, the apical cuff axial compression attachment assembly 100, 200 is first affixed to the heart through deployment of the tissue anchors 30. Thereafter, a core of ventricular muscle is removed from the center of the apical cuff 10, 20, and an LVAD pump inlet cannula is introduced into the ventricular cavity, and the LVAD is mechanically coupled to the apical cuff 20.

Figure 23:
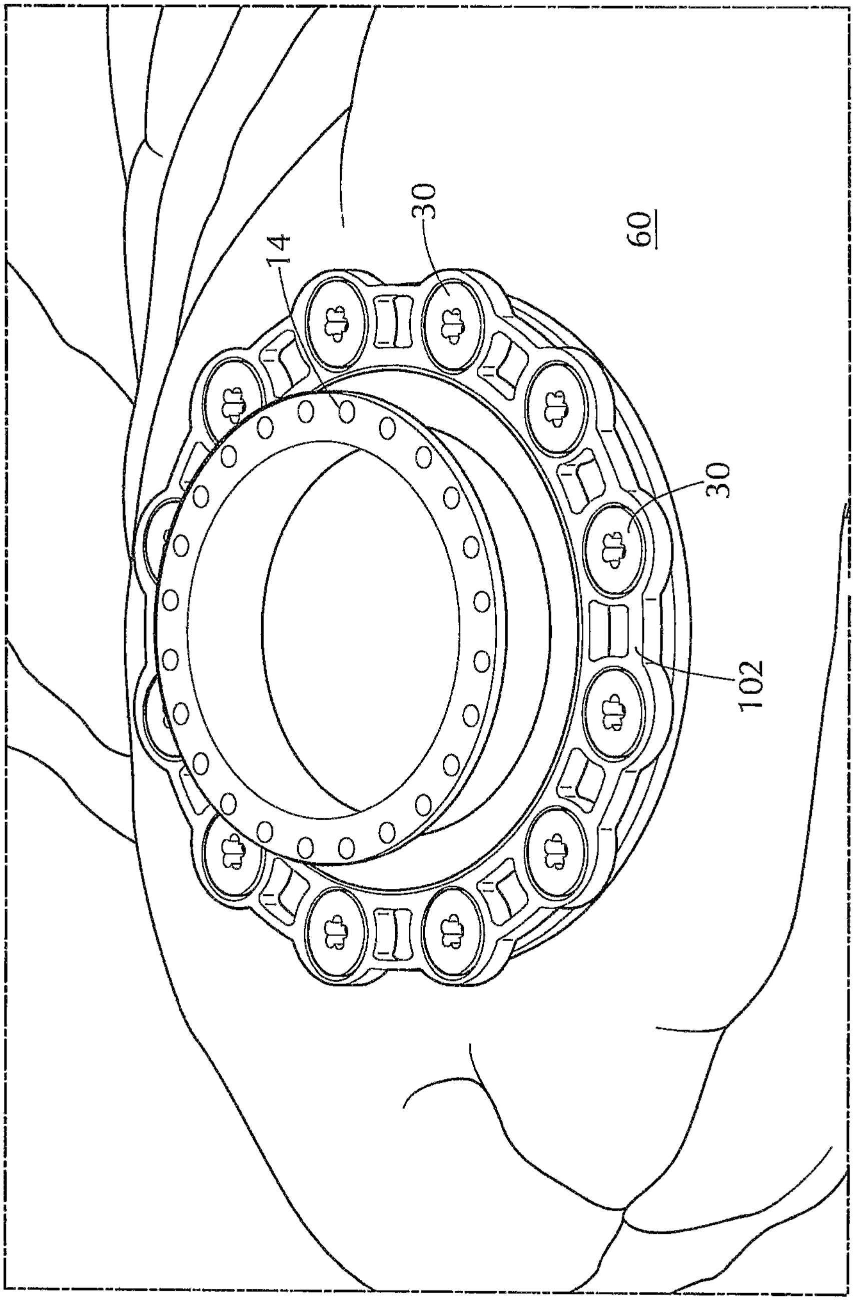
FIG. 23 is a perspective view of the first embodiment of the present disclosure with an apical cuff, axial compression ring member and helical screws experimentally affixed to a chicken breast.
Figure 24:
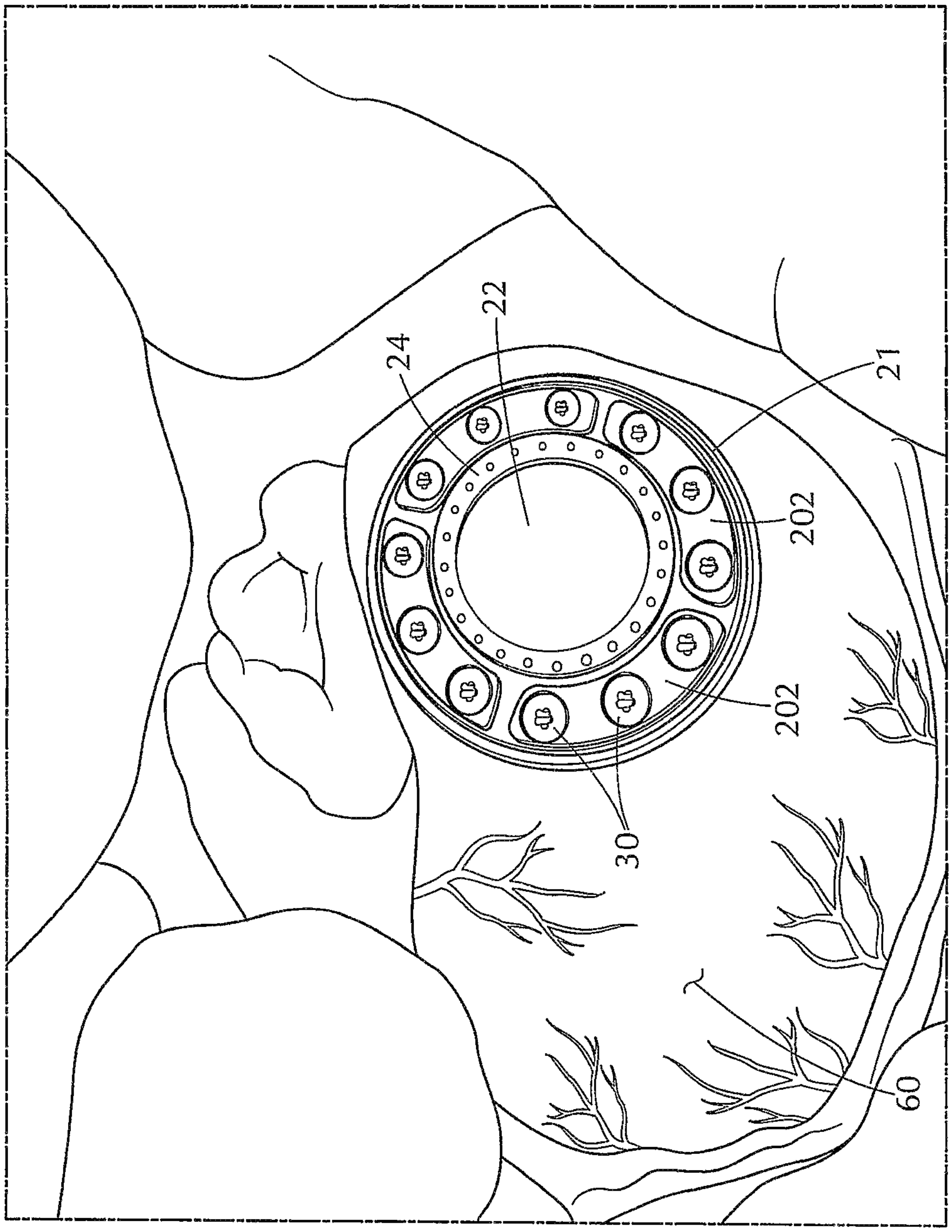
FIG. 24 is a perspective view of an apical cuff, axial compression plates and helical screws joined experimentally to a bovine heart in accordance with a second embodiment of the present disclosure.

FIG. 23 illustrates an apical cuff 10 and apical cuff axial compression attachment assembly 100 joined to a chicken breast simulating heart muscle, 60. FIG. 24 illustrates an apical cuff 20 and axial compression attachment assembly 200 joined to a bovine heart muscle.

Figure 25:
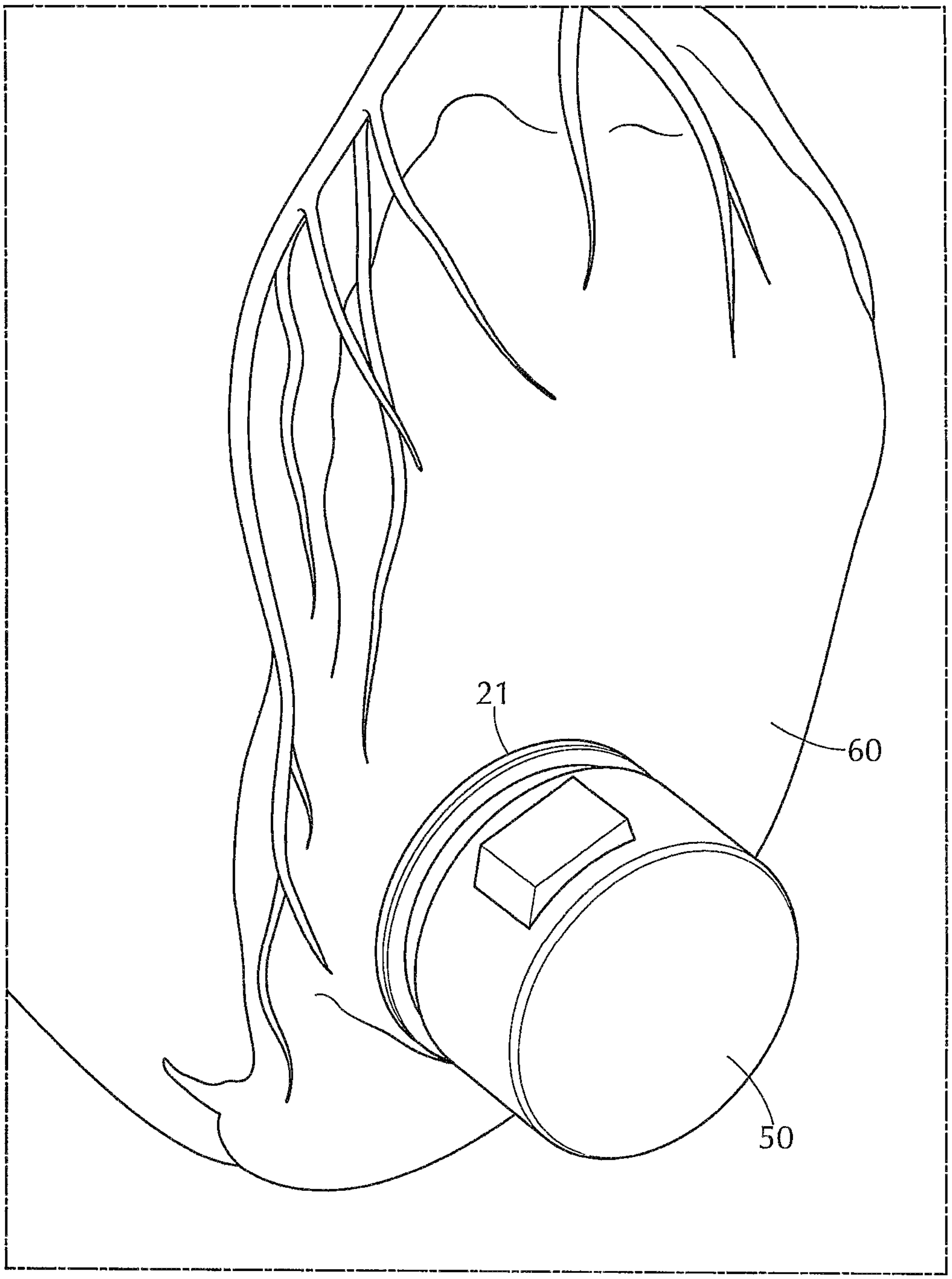
FIG. 25 is a perspective view illustrating attachment of a VAD pump to an apical cuff joined to a heart with the apical cuff axial cuff attachment assembly in accordance with either the first or second embodiment of the present disclosure.

As illustrated in FIG. 25, once the apical cuff 10, 20 and apical cuff axial compression assembly 100, 200 is joined to the heart muscle 60 and the heart muscle is cored, the VAD pump 50 may then be connected to coupling flange 14, 24 of the apical cuff 10, 20, respectively, depending upon which apical cuff is employed.

While the present disclosure has been made with reference to the accompanying Figures and exemplary and alternative embodiments or variants of the present invention, it will be understood that the present disclosure is not intended to be limited only to the described elements, embodiments, materials, methods, assemblies, structures, dimensions, geometries or the like. Rather, the scope of the present disclosure is intended to be restricted only by the claims appended hereto. Variations in sizes, shapes, geometries, combinations, assemblies, materials or the like are expressly contemplated by the present disclosure.

What is claimed is:

1. An axial compression assembly for affixation to anatomical tissue, comprising:

a plurality of tissue anchors;

a sewing skirt comprising an annular ring having absorptive and/or hemostatic properties; and at least one axial compression member defining a central opening and having a plurality of tissue anchor openings passing axially through the at least one axial compression member and circumferentially spaced about the at least one axial compression member, the plurality of tissue anchors passing into and through the plurality of tissue anchor openings and bearing upon the at least one axial compression member, the sewing skirt, and the anatomic tissue, thereby applying an axially compressive force distributed substantially evenly about a circumference of the at least one axial compression member.

2. The axial compression assembly of claim 1, wherein the at least one axial compression member further comprises at least one of a plurality of secondary openings, the secondary openings having a different opening configuration than the plurality of tissue anchor openings.

3. The axial compression assembly of claim 1, wherein each of the plurality of tissue anchors further comprises a tissue anchor head having a driver engagement at a proximal surface of the tissue anchor head and a helical coil projection from a distal surface of the tissue anchor head.

4. The axial compression assembly of claim 3, wherein the tissue anchor head further has distally tapered side walls.

5. The axial compression assembly of claim 4, wherein each of the plurality of openings further has a tapered opening profile having a taper that mate with the distally tapered side walls of the tissue anchor head.

6. The axial compression assembly of claim 1, wherein each of the plurality of openings is positioned to allow the plurality of tissue anchors to pass axially into and through the annular ring of the sewing skirt.

7. The axial compression assembly of claim 1, further comprising a loading tray.

8. The axial compression assembly of claim 1, further comprising a delivery tool.

9. An assembly configured for affixation to anatomical tissue, comprising, in combination:

a plurality of tissue anchors;

a sewing skirt comprising an annular ring having absorptive and/or hemostatic properties;

at least one axial compression member configured to define a central opening and having a plurality of tissue anchor openings passing axially through the at least one axial compression member and circumferentially spaced about the at least one axial compression member, the plurality of tissue anchors passing into and through the plurality of tissue anchor openings and bearing upon the at least one axial compression member, the sewing skirt, and the anatomic tissue, thereby applying an axially compressive force distributed substantially evenly about a circumference of the at least one axial compression member; and a delivery tool removably coupled to the axial compression assembly with a delivery tool housing that retains each of the plurality of tissue anchors in a corresponding delivery tool channel in the delivery tool housing until release of the plurality of tissue anchors from the corresponding delivery tool channel and coupling the plurality of tissue anchors to anatomic tissue.

10. The assembly of claim 9, further comprising an apical cuff coupled to the axial compression assembly.

11. The assembly of claim 10, wherein the plurality of tissue anchors each further includes an indicia associated with a driver engagement, the indicia being in axial alignment with a distal tip of each of the plurality of tissue anchors.

12. The assembly of claim 10, wherein the apical cuff further includes the sewing skirt, and the plurality of tissue anchors pass into the sewing skirt when the apical cuff is coupled to the axial compression assembly.

13. The assembly of claim 10, further including a loading tray.

14. The assembly of claim 13, wherein the loading tray, the apical cuff, the axial compression assembly and the delivery tool are removably coupled to each other.

15. An apical cuff axial compression assembly for affixation of an apical cuff having a sewing skirt to cardiac tissue, comprising:

at least one member configured to define an annular ring having a central opening and having a plurality of openings positioned in a spaced apart relation about at least a substantial circumferential extent of the annular ring, the at least one member configured to bear against the sewing skirt; and a plurality of tissue screws, each of the plurality of tissue screws having a tissue screw head and a helical coil projecting from the tissue screw head, wherein each of the plurality of tissue screws are configured to pass into and through the plurality of openings, the sewing skirt and into cardiac tissue, and exert an axially compressive force onto the ring member, the sewing skirt, and the cardiac tissue as a primary securement of the apical cuff to the cardiac tissue.

16. The apical cuff axial compression assembly of claim 15, wherein the plurality of tissue anchor openings are positioned radially inward from an outer perimeter of the sewing skirt.

17. The apical cuff axial compression assembly of claim 15, wherein the helical coil has a first helical pitch at a proximal end thereof and a second helical pitch at a distal end thereof.

18. The apical cuff axial compression assembly of claim 17, wherein the second helical pitch is greater than the first helical pitch.

19. The apical cuff axial compression assembly of claim 18, wherein a diameter of the helical coil is substantially the same as a diameter of the tissue screw head.

* * * * *